United States Patent [19]

Hüsler et al.

[11] Patent Number: 4,739,052

[45] Date of Patent: Apr. 19, 1988

[54] PHENYL KETONE DERIVATIVES

[75] Inventors: Rinaldo Hüsler, Basel; Rudolf Kirchmayr, Aesch; Werner Rutsch, Fribourg, all of Switzerland

[73] Assignee: Ciba-Geigy Corporation, Ardsley, N.Y.

[21] Appl. No.: 783,377

[22] Filed: Oct. 2, 1985

Related U.S. Application Data

[62] Division of Ser. No. 579,622, Feb. 13, 1984, Pat. No. 4,559,371.

[30] Foreign Application Priority Data

Feb. 18, 1983 [CH] Switzerland ............................ 903/83

[51] Int. Cl.$^4$ ..................... C07C 97/10; C07D 295/10
[52] U.S. Cl. .................................... 544/174; 544/175; 544/399; 546/237; 564/344; 564/305; 564/337; 564/339
[58] Field of Search ................ 544/174; 564/344, 305, 564/337, 339

[56] References Cited

U.S. PATENT DOCUMENTS 4,308,400 12/1981 Felder et al. ......................... 564/344

*Primary Examiner*—Robert W. Ramsuer
*Attorney, Agent, or Firm*—Luther A. R. Hall

[57] ABSTRACT

Compounds of the formula I, II or III

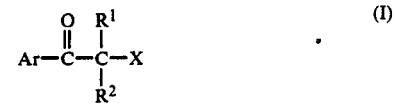

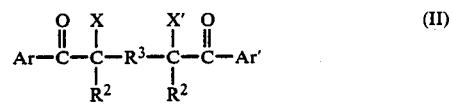

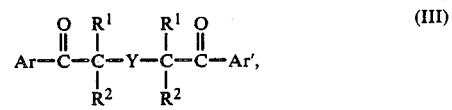

in which Ar and Ar' are an oxygen-containing aromatic radical, $R^1$ and $R^2$ are a monovalent hydrocarbon radical which is substituted or unsubstituted, or $R^1$ and $R^2$ together form alkylene, oxaalkylene or azaalkylene, $R^3$ is a direct bond or a divalent hydrocarbon radical, X and X' are a monovalent amino group and Y is a divalent amino or diamino group, are excellent photoinitiators for the photocuring of colored, especially pigmented, compositions containing an olefinically unsaturated, photopolymerizable binder.

4 Claims, No Drawings

PHENYL KETONE DERIVATIVES

This is a divisional of application Ser. No. 579,622 filed on Feb. 13, 1984, now U.S. Pat. No. 4,559,371.

The invention relates to photocurable coloured compositions containing an olefinically unsaturated binder, a pigment or a dye and a specific photoinitiator. The photoinitiator is an aromatic-aliphatic ketone which contains, in the aromatic moiety, one or more hydroxyl or ether groups and contains, in the aliphatic moiety, a tertiary α-C atom on which an amino group is located.

It is known that photoinitiators are added before irradiation in order to accelerate the photocuring of coloured compositions, for example printing inks or paints. This renders it possible to cure such compositions in a very short time of irradiation sufficiently for their surface to be no longer tacky. Whereas there are a number of technically satisfactory photoinitiators for transparent coating compositions, the radiation curing of coloured compositions constitutes a problem particularly difficult to solve because of the presence of the light-absorbing pigments or dyes. In the case of printing inks there is also the requirement for extremely short curing times because of the high speed of modern printing machines. The requirements for photoinitiators for coloured compositions are therefore considerably higher than those for transparent photocurable compositions.

Photoinitiators which have hitherto been used in the art for the curing of such coloured compositions, for example printing inks or paints, are in most cases synergistic mixtures of ketonic photoinitiators with specific amines, for example a mixture of benzophenone with Michler's ketone (4,4'-bis-dimethylaminobenzophenone) or with alkyl p-dimethylaminobenzoates, or mixtures of thioxanthones with N-methyldiethanolamine. Ketone-amine mixtures of this type tend to undergo yellowing in light. This can manifest itself as early as the radiation curing, but at the latest when the cured layers are exposed to the prolonged action of light. Some of these compounds are difficultly soluble in the customary acrylic resin binders, then to recrystallise and considerably shorten the storage life of the mixture. Other compounds of this type, for example the alkanolamines, are soluble in water and therefore cannot be used for wet offset printing inks. Furthermore, the ketone-amine mixtures act in accordance with a bimolecular initiation mechanism which is controlled by diffusion and therefore takes place relatively slowly in systems of high viscosity.

Molecular combinations of aryl ketones and amines in which the amino group is located on a tertiary C atom in the α-position in relation to the carbonyl group have already been suggested as photoinitiators in European Patent Application, Publication No. 3002. However, the aminoketones described in this text have proved inferior as photoinitiators in clear lacquers to the corresponding hydroxyketones described in the same patent specification. The hydroxyketones described in this text are admittedly excellent initiators for transparent lacquers, but exhibit only a moderately good action in pigmented compositions, for example in printing inks.

It has been found that such aminoketones which carry at least one hydroxyl or ether group on the aromatic nucleus surprisingly exhibit an excellent initiator action in coloured compositions, especially in printing inks, and do not have the disadvantages of the ketone-amine mixtures or have these disadvantages to a considerably lesser extent.

The invention relates therefore to photocurable coloured compositions containing:
(a) an olefinically unsaturated, photopolymerisable binder,
(b) a pigment or a dye and
(c) as photoinitiator, at least one compound of the formula I, II or III

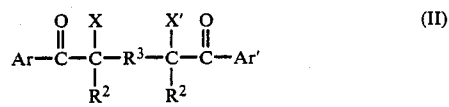

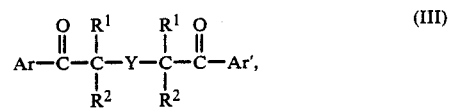

in which Ar is an oxygen-containing aromatic radical, selected from the following formulae:

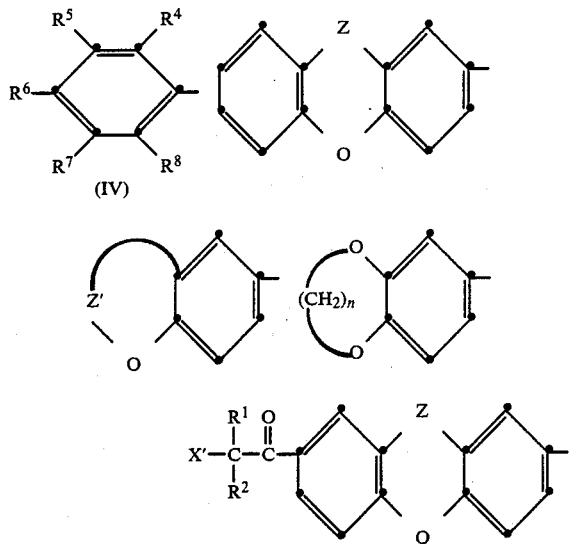

wherein
n is 1, 2 or 3,
Z is a direct bond, —CH$_2$—, —CH$_2$CH$_2$— or —O—,
Z' is 13 CH$_2$CH$_2$— or —(CH$_2$)$_3$, each unsubstituted or substituted by CH$_3$,
R$^4$, R$^5$, R$^6$, R$^7$ and R$^8$ independently of one another are each hydrogen, halogen, C$_1$–C$_4$-alkyl, C$_3$–C$_{12}$-alkenyl, C$_5$–C$_6$-cycloalkyl, phenyl, —COOH, —COO(C$_1$–C$_4$-alkyl), —OH or —OR$^9$, with the proviso however that at least one of the radicals R$^4$ to R$^8$ is an —OH or —OR$^9$ group,
R$^9$ is C$_1$–C$_{12}$-alkyl, C$_3$–C$_{12}$-alkenyl, cyclohexyl, hydroxycyclohexyl, C$_1$–C$_4$-alkyl which is substituted by one or more of the groups Cl, Br, CN, SH, —N(C$_1$–C$_4$-alkyl)$_2$, piperidino, morpholino, OH, —O(C$_1$–C$_4$-alkyl), —OCH$_2$CH$_2$CN, —OCH$_2$CH$_2$COO(C$_1$–C$_4$-alkyl), —OOC—R$^{10}$, —COOH, —COO(C$_1$–C$_8$- alkyl), —CONH($C_1$-$C_4$-alkyl), —CON($C_1$-$C_4$-alkyl)$_2$,

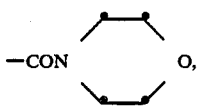

—CO—($C_1$-$C_4$-alkyl) or —CO—phenyl, or is 2,3-epoxypropyl, —(CH$_2$CH$_2$O)$_q$—H, phenyl, $C_7$-$C_9$-phenylalkyl, $C_7$-$C_9$-phenylhydroxyalkyl, phenyl which is substituted by halogen, $C_1$-$C_4$-alkyl, $C_1$-$C_4$-alkoxy or —COO($C_1$-$C_4$-alkyl), or is tetrahydropyranyl, tetrahydrofuranyl, a group —CO—$R^{10}$, —COO($C_1$-$C_8$-alkyl), —CONH($C_1$-$C_4$-alkyl), —CON($C_1$-$C_4$-alkyl)$_2$, —Si($R^{15}$)($R^{16}$)$_2$, —SO$_2$—$R^{17}$ or a radical of the formula

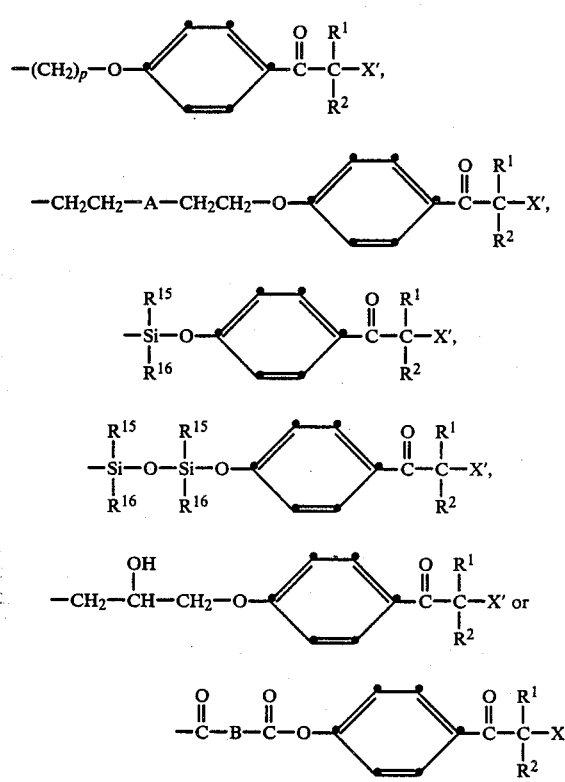

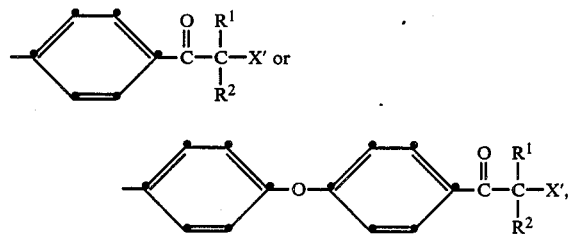

wherein p is 1 to 4, q is 2 to 20, A is oxygen or sulfur and B is a direct bond or a $C_1$-$C_{10}$-alkylene radical, or R$_9$ is a radical of the formula $R^{10}$ is $C_1$-$C_4$-alkyl, $C_2$-$C_4$-alkenyl or phenyl,
X and X' are each an amino group —N($R^{11}$)($R^{12}$),
Y is a divalent radical of the formula

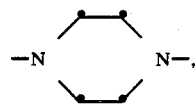

—N($R^{13}$)— or —N($R^{13}$)—(CH$_2$)$_x$—N($R^{13'}$)—, wherein x is 1 to 8, $R^{11}$ is hydrogen, $C_1$-$C_{12}$-alkyl, $C_2$-$C_4$-alkyl which is substituted by one or more of the groups OH, $C_1$-$C_4$-alkoxy, CN or —COO($C_1$-$C_4$-alkyl), or is $C_3$-$C_5$-alkenyl, cyclohexyl, $C_7$-$C_9$-phenylalkyl, phenyl or phenyl substituted by Cl, $C_1$-$C_4$-alkyl, OH, $C_1$-$C_4$-alkoxy or —COO($C_1$-$C_4$-alkyl), or $R^{11}$ and $R^1$ together are the group —CH$_2$OCH$_2$—, $R^{12}$ has one of the meanings given for $R^{11}$ or together with $R^{11}$ is $C_3$-$C_7$-alkylene which can be interrupted by —O—, —S— or —N($R^{14}$)—, or $R^{12}$ together with $R^2$ is $C_1$-$C_8$-alkylene, $C_7$-$C_{10}$-phenylalkylene, o-xylylene or $C_2$-$C_4$-oxa or azaalkylene, $R^{13}$ and $R^{13'}$ are hydrogen, $C_1$-$C_{12}$-alkyl, $C_1$-$C_4$-hydroxyalkyl, cyclohexyl or benzyl, $R^{14}$ is hydrogen, $C_1$-$C_4$-alkyl, $C_1$-$C_4$-hydroxyalkyl, —CH$_2$CH$_2$CN or —CH$_2$CH$_2$COO($C_1$-$C_4$-alkyl), $R^{15}$ and $R^{16}$ are $C_1$-$C_4$-alkyl or phenyl, $R^{17}$ is $C_1$-$C_{18}$-alkyl, phenyl or $C_7$-$C_{20}$-alkylphenyl, Ar' has one of the meanings given for Ar, $R^1$ and $R^2$ independently of one another are each $C_1$-$C_8$-alkyl, $C_1$-$C_4$-alkyl which is substituted by OH, $C_1$-$C_4$-alkoxy, CN, —COO($C_1$-$C_8$-alkyl) or —N($R^{11}$)($R^{12}$), or are allyl, phenyl, chlorophenyl, $R^9$—O—phenyl or $C_7$-$C_9$-phenylalkyl, or $R^1$ and $R^2$ together are $C_2$-$C_8$-alkylene, $C_3$-$C_9$-oxa- or azaalkylene, $R^3$ is a direct bond, $C_1$-$C_6$-alkylene, $C_2$-$C_6$-oxaalkylene or cyclohexylene, or together with the two substituents $R^2$ and the two C atoms to which they are attached forms a cyclopentane, cyclohexane, cyclohexene, endomethylenecyclohexane or endomethylenecyclohexene ring, or to an acid addition salt of such a compound.

As alkyl, $R^9$ can be therein straight-chain or branched-chain alkyl, for example: methyl, ethyl, isopropyl, n-butyl, isobutyl, tert-butyl, isoamyl, n-hexyl, n-octyl, 2-ethylhexyl, n-decyl or n-dodecyl.

As alkenyl, $R^9$ can be in particular alkenyl-methyl, for example allyl, methallyl or 11-undecenyl.

As substituted alkyl, $R^9$ can be for example: 2-chloroethyl, 2-bromomethyl, 3-chloropropyl, cyanomethyl, 2-cyanoethyl, 2-mercaptoethyl, dimethylaminomethyl, morpholinomethyl, 2-piperidinoethyl, 2-morpholinoethyl, 2-hydroxyethyl, 2-hydroxypropyl, 2-butoxyethyl, 2-ethoxybutyl, 2-(2'-cyanoethoxy)-propyl, 2-(2'-ethoxycarbonylethoxy)-ethyl, 2-acetoxyethyl), 2-acryloyloxypropyl, 2-benzoyloxyethyl, carboxymethyl, 2-methoxycarbonylethyl, butoxycarbonylmethyl, n-octyloxycarbonylmethyl, 2-diethylcarbamoylethyl, morpholinocarbonylmethyl, 2-isobutyroylethyl, 2-benzoylethyl or acetylmethyl.

When $R^9$ is phenylalkyl or phenylhydroxyalkyl, this can be for example: benzyl, phenylethyl, phenylpropyl or 2-phenyl-2-hydroxyethyl.

$R^9$ as substituted phenyl can be for example: 4-chlorophenyl, 3-bromophenyl, 2-fluorophenyl, p-tolyl, p-isopropylphenyl, 2,4-dimethylphenyl, 4-methoxyphenyl, 3-ethoxy-p-tolyl, 3-methoxycarbonylphenyl or 4-butoxycarbonyl-phenyl.

X can be a primary, secondary or tertiary amino group; preferably however X is a tertiary amino group. The substituents $R^{11}$ and $R^{12}$ can be aliphatic, cycloaliphatic aromatic or araliphatic groups. Examples of $R^{11}$ and $R^{12}$ are the groups: methyl, ethyl, propyl, butyl, hexyl, octyl, 2-ethylhexyl, dodecyl, 2-hydroxyethyl, 2-hydroxypropyl, 2-hydroxybutyl, 2-methoxypropyl, 2-ethoxyethyl, 2-cyanoethyl, 2-methoxycarbonylethyl, ethoxycarbonylmethyl, 2-isopropoxycarbonylethyl, allyl, methallyl, cyclohexyl, benzyl, phenylethyl, phenyl, 4-chlorophenyl, 4-tolyl, 3-hydroxyphenyl, 3-methoxyphenyl, 4-ethoxyphenyl, 4-methoxycarbonylphenyl or 2,4-dimethylphenyl. When $R^{11}$ and $R^{12}$ together are alkylene or interrupted alkylene, X can be for example: a pyrrolidino, oxazolidino, piperidino, 3,5-dimethylpiperidino, morpholino, 3,5-dimethyl-morpholino, thiomorpholino, piperazino, 4-methyl-piperazino, 4-(cyanoethyl)-piperazino or 4-(hydroxyethyl)piperazino group. When $R^{12}$ together with $R^2$ forms an alkylene, phenylalkylene, o-xylylene, oxaalkylene or azaalkylene radical, these can form, together with the C atom to which $R^2$ and $R^{12}$ are attached, for example an aziridine, pyrrolidine, piperidine, tetrahydroisoquinoline, phenylaziridine, methylpyrrolidine, dimethylpiperidine or morpholine ring. When $R^{11}$ and $R^1$ together are —$CH_2OCH_2$—, these radicals together with the nitrogen atom and the quaternary carbon atom form an oxazolidine ring. If $R^{12}$ and $R^2$ also form an oxazolidine ring of this type, this results in compounds of the formula

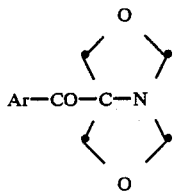

X is preferably a morpholino radical or a radical of the formula —$N(CH_2CH_2OCH_3)_2$. Y is a divalent secondary or tertiary amino or diamino group. Examples of diamino groups —$N(R^{13})$—$(CH_2)_x$—$N(R^{13'})$— are in particular those in which $x = 1, 2, 3, 4$ and 6. As $C_1$-$C_{10}$-alkylene, B can be a straight-chain or branched chain alkylene group, for example methylene, di-, tri-, tetra-, hexa-, octa-, decamethylene, 1,3,3-trimethylbutylene-1,4, pentylene-3,3 or 2-ethylpropylene-1,3.

As alkyl or substituted alkyl, $R^1$ and $R^2$ can be for example: methyl, ethyl, propyl, butyl, isopentyl, hexyl, isooctyl, hydroxymethyl, methoxymethyl, 2-cyanoethyl, 2-methoxycarbonylethyl, 2-butoxycarbonylethyl, dimethylaminomethyl or 3-aminopropyl. When $R^1$ and $R^2$ together are alkylene, oxaalkylene or azaalkylene, they form, together with the C atom to which they are attached, for example a cyclopentane, cyclohexane, cyclooctane, tetrahydropyrane, pyrrolidine or piperidine ring. $R^1$ and $R^2$ are preferably $C_1$-$C_4$-alkyl, especially methyl, or $R^1$ and $R^2$ together are $C_{2-C8}$-alkylene, particularly pentamethylene.

As alkylene, $R^3$ can be a straight-chain or branched-chain alkylene radical, for example methylene, ethylene, tri, tetra-, penta- or hexamethylene, 2,2-dimethylpropylene-1,3 or 2,3-dimethylbutylene-1,4. As oxaalkylene, $R^3$ can be for example 2-oxapropylene-1,3 or 3-oxapentylene-1,5.

$R^4$, $R^5$, $R^6$, $R^7$ and $R^8$ can be $C_1$-$C_4$-alkyl, for example: methyl, ethyl, isopropyl, n-butyl or sec-butyl.

These radicals can also be $C_3$-$C_{12}$-alkenyl, especially alkenylmethyl, for example allyl, methallyl or 11-undecenyl. Furthermore, these radicals can be $C_5$-$C_6$-cycloalkyl, such as cyclopentyl or cyclohexyl.

$R^{10}$ can be for example: methyl, ethyl, propyl, butyl, vinyl, propenyl, butenyl or phenyl.

As $C_1$-$C_{12}$-alkyl, $R^{13}$ can be one of the alkyl groups given for $R^9$. As $C_1$-$C_4$-hydroxyalkyl, $R^{13}$ and $R^{14}$ can be for example hydroxymethyl, 2-hydroxyethyl, 2-hydroxypropyl or 2-hydroxybutyl.

As $C_1$-$C_4$-alkyl, $R^{15}$ and $R^{16}$ are in particular methyl; $R^{17}$ as $C_1$-$C_{18}$-alkyl can be for example: methyl, propyl, tert-butyl, 2-ethylhexyl, n-dodecyl or n-octadecyl. As $C_7$-$C_{20}$-alkylphenyl, $R^{17}$ can be for example: tolyl, butylphenyl, octylphenyl, nonylphenyl or dodecylphenyl. $R^{17}$ can also be a technical mixture of various alkyl or alkylphenyl radicals.

Preferred photoinitiators are compounds of the formula I, II or III in which Ar is a radical of the formula IV wherein at least one of the radicals $R^4$ to $R^8$ is a group —OH— or —$OR^9$. This group is preferably in the 4-position. The remaining positions of the phenyl radical can be unsubstituted or they can likewise carry a group —$OR^9$ or some other of the substituents $R^4$ to $R^8$ defined above. $R^9$ corresponds to the definition given in the foregoing.

Further preferred photoinitiators are in particular compounds of the formula I in which Ar is a phenyl radical which is substituted by 1 or 2 of the groups —OH or $OR^9$, $R^9$ is $C_1$-$C_{12}$-alkyl, $C_3$-$C_6$-alkenyl, cyclohexyl, $C_7$-$C_9$-phenylalkyl, phenyl, phenyl substituted by $C_1$-$C_4$-alkyl, or is tetrahydropyranyl or one of the groups —$CH_2CH_2OH$, —$CH_2C$-$H_2$—$OOC$—$CH=CH_2$, —$CH_2CN$, —$CH_2COOH$, —$CH_2COO(C_1$-$C_8$-alkyl), —$CH_2CH_2CN$, —$CH_2CH_2COO(C_1$-$C_8$-alkyl), —$(CH_2CH_2O)_q$—H, —$Si(R^{15})(R^{16})_2$,

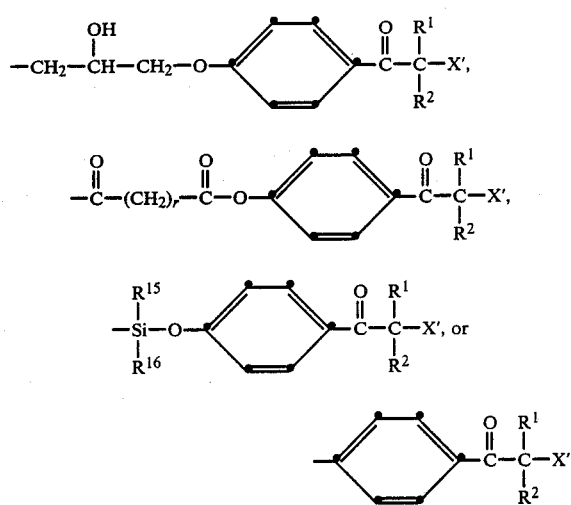

in which
q is 2 to 10 and r is 2 to 8,
$R^1$ and $R^2$ independently of one another are each $C_1$-$C_4$-alkyl, phenyl or $C_7$-$C_9$-phenylalkyl, or $R^1$ and $R^2$ together are $C_2$-$C_8$-alkylene, and
X and X' are identical and are an amino group —$N(R^{11})(R^{12})$ wherein $R^{11}$ is $C_1$-$C_8$-alkyl, $C_2$-$C_4$-alkyl substituted by OH, $C_1$-$C_4$-alkoxy or CN, or is C₃–C₅-alkenyl, and R¹² has one of the meanings given for R¹¹, or together with R¹¹ is C₄–C₆-alkylene which can be interrupted by —O—, —S— or N(R¹⁴)—, wherein R¹⁴ is C₁–C₄-alkyl, 2-cyanoethyl, 2-hydroxyethyl or 2-hydroxypropyl.

Particularly preferred photoinitiators are compounds of the formula I
wherein
Ar is a phenyl radical substituted in the 4-position by a group —OR⁹,
R⁹ is C₁–C₈-alkyl, C₃–C₆-alkenyl, cyclohexyl, benzyl, phenyl, tolyl or one of the groups: —CH₂CH₂OH, —CH₂CH₂—OOC—CH=CH₂, —CH₂—COO(C₁–C₄-alkyl), —CH₂CH₂—COO(C₁–C₄-alkyl),

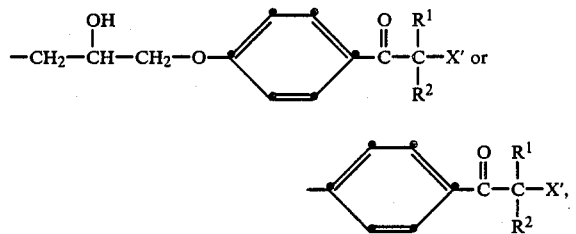

R¹ and R² are C₁–C₄-alkyl, or R¹ and R² together are C₄–C₅-alkylene, and
X and X' are a morpholino radical or a radical of the formula —N(CH₂CH₂OCH₃)₂.

Examples of photoinitiators of the formula I which can be used according to the present invention are the following compounds:

1-(4-methoxyphenyl)-2-methyl-2-morpholinopropanone-1,
2-methyl-1-(4-phenoxyphenyl)-2-morpholinopropanone-1,
1-(4-methoxyphenyl)-2-methyl-2-piperidinopropanone-1,
2-methyl-1-(4-phenoxyphenyl)-2-piperidinopropanone-1,
1-(4-ethoxyphenyl)-2-methyl-2-morpholinopropanone-1,
1-(4-isopropoxyphenyl)-2-methyl-2-morpholino-propanone-1,
1-(4-butoxyphenyl)-2-methyl-2-morpholinopropanone-1,
1-(4-octyloxyphenyl)-2-methyl-2-morpholinopropanone-1,
1-(4-dodecyloxyphenyl)-2-methyl-2-morpholinopropanone-1,
1-(4-hydroxyphenyl)-2-methyl-2-morpholinopropanone-1,
1-(4-acetoxyphenyl)-2-methyl-2-morpholinopropanone-1,
1-(4-isobutyryloxyphenyl)-2-methyl-2-morpholinopropanone-1,
1-(4-acrylyloxyphenyl)-2-methyl-2-morpholinopropanone-1,
1-(4-benzoxyphenyl)-2-methyl-2-morpholinopropanone-1,
1-(4-ethoxycarbonyloxyphenyl)-2-methyl-2-morpholinopropanone-1,
1-(4-methoxycarbonyloxyphenyl)-2-methyl-2-morpholinopropanone-1,
1-(4-N-ethylcarbamoyloxyphenyl)-2-methyl-2-morpholinopropanone-1,
1-(4-N,N-dimethylcarbamoyloxyphenyl)-2-methyl-2-morpholinopropanone-1,
1-(4-N,N-diethylcarbamoyloxyphenyl)-2-methyl-2-morpholinopropanone-1,
1-[4-(2-tetrahydropyranyloxy)phenyl]-2-methyl-2-morpholinopropanone-1,
1-[4-(2-tetrahydrofuranyloxy)phenyl]-2-methyl-2-morpholinopropanone-1,
1-[4-trimethylsilyloxy)phenyl]-2-methyl-2-morpholinopropanone-1,
1-[4-(triethylsilyloxy)phenyl]-2-methyl-2-morpholinobutanone-1,
1-[4-(tert.-butyldimethylsilyloxy)phenyl]-2-methyl-2-morpholinopropanone-1,
1-[3-(dimethylphenyl-silyloxy)phenyl]-2-methyl-2-morpholinopropanone-1,
1-[4-(diphenyl-tert.-butylsilyloxy)phenyl]-2-ethyl-2-morpholinobutanone-1,
1-[4-(diphenylmethylsilyloxy)phenyl]-2-ethyl-2-morpholinohexanone-1,
1-[4-(methylsulfonyloxy)phenyl]-2-methyl-2-morpholinopropanone-1,
1-[4-(dodecylsulfonyloxy)phenyl]-2-methyl-2-morpholinopropanone-1,
1-[4-(octadecylsulfonyloxy)phenyl]-2-methyl-2-morpholinopropanone-1,
1-[3-(phenylsulfonyloxy)phenyl]-2-methyl-2-morpholinopropanone-1,
1-[4-(p-tolylsulfonyloxy)phenyl]-2-methyl-2-morpholinopropanone-1,
1-[4-(p-dodecylphenylsulfonyloxy)phenyl]-2-methyl-2-morpholinopropanone-1,
1-[4-(allyloxy)phenyl]-2-methyl-2-morpholinopropanone-1,
1-[4-(2-butenyloxy)phenyl]-2-methyl-2-morpholinopropanone-1,
1-(4-cyclohexyloxyphenyl)-2-methyl-2-morpholinopropanone-1,
1-[4-(2-hydroxycyclohexyloxy)phenyl]-2-methyl-2-morpholinopropanone-1,
1-[4-(2,3-dihydroxypropyloxy)phenyl]-2-methyl-2-morpholinopropanone-1,
1-[4-(2,3-epoxypropyloxy)phenyl]-2-methyl-2-morpholinopropanone-1,
1-[4-(2-hydroxyethoxy)phenyl]-2-methyl-2-morpholinopropanone-1,
1-[4-(2-(2-hydroxyethoxy)ethoxy)phenyl]-2-methyl-2-morpholinopropanone-1,
1-[3-(8-hydroxy-3,6-dioxaoctyloxy)phenyl]-2-methyl-2-morpholinopropanone-1,
1-[4-(29-hydroxy-3,6,9,12,15,18,21,24,27-nonaoxanonacosyloxy)phenyl]-2-methyl-2-morpholinopropanone-1,
1-[4-(53-hydroxy-3,6,9,12,15,18,21,24,27,30,33,36,39,42,45,48,51-heptadecaoxatripentacontyloxy)phenyl]-2-methyl-2-morpholinopropanone-1,
1-[4-(benzyloxy)phenyl]-2-methyl-2-morpholinopropanone-1,
1-[4-(2-hydroxy-2-phenyl-ethoxy)phenyl]-2-methyl-2-morpholinopropanone-1,
1-[4-(2-methoxyethoxy)phenyl]-2-methyl-2-morpholinopropanone-1,
1-[3(2-butoxyethoxy)phenyl]-2-methyl-2-morpholinopropanone-1,
1-[2-[3-chloropropyloxy)phenyl]-2-methyl-2-morpholinopropanone-1, 1-[4-(4-bromobutyloxy)phenyl]-2-methyl-2-morpholinopropanone-1,
1-[4-(2-cyanoethoxy)phenyl]-2-methyl-2-morpholinopropanone-1,
1-[4-(3-dimethylaminopropyloxy)phenyl]-2-methyl-2-morpholinopropanone-1,
1-[4-(2-morpholinoethoxy)phenyl]-2-ethyl-2-morpholinohexanone-1,
1-[4-(2-ethoxycarbonylethoxy)phenyl]-2-ethyl-2-morpholinobutanone-1,
1-[4-(2-acryloyloxyethoxy)phenyl]-2-methyl-2-morpholinopropanone-1,
1-[4-(carboxymethoxy)phenyl]-2-methyl-2-morpholinopentanone-1,
1-[4-(2-ethylhexyloxycarbonylmethoxy)phenyl]-2-methyl-2-morpholinopropanone-1,
1-[4-(3-morpholino-3-oxopropyloxy)phenyl]-2-methyl-2-morpholinopropanone-1,
1-[4-(2-oxopropyloxy)phenyl-2-methyl-2-morpholinopropanone-1,
2-methyl-1-(4-tolyloxyphenyl)-2-morpholinopropanone-1,
2-methyl-1-[4-(phenethyloxy)phenyl]-2-morpholinopropanone-1,
1-[4-(4-chlorophenoxy)phenyl]-2-methyl-2-morpholinopropanone-1,
1-[4-(2-carbethoxyphenoxy)phenyl]-2-methyl-2-morpholinopropanone-1,
1-(2-methyl-4-phenoxyphenyl)-2-methyl-2-morpholinopropanone-1,
1-[3-isopropyl-4-(4-isopropylphenoxy)phenyl]-2-methyl-2-morpholinopropanone-1,
1-[4-(3-dimethylamino-2-hydroxypropyloxy)phenyl]-2-methyl-2-morpholinopropanone-1,
1-[3-(2-(2-cyanoethoxy)ethoxy)phenyl]-2-methyl-2-morpholinopropanone-1,
1-[4-(3-mercaptopropyloxy)-3-methylphenyl]-2-methyl-2-morpholinopropanone-1,
1-(4-anisoyl)-1-morpholinocyclohexane,
1-(4-ethoxybenzoyl)-morpholinocyclohexane,
1-(3-cyclohexyl-4-methoxybenzoyl)-1-morpholinocyclohexane,
1-(2-allyl-4,5-dimethoxyphenyl)-2-methyl-2-morpholinopropanone-1,
1-[4-(2-chloro-3-methoxyphenoxy)phenyl]-2-methyl-2-morpholinopropanone-1,
1-[4-(2,4-dibromophenoxy)phenyl]-2-methyl-2-morpholinopropanone-1,
bis[4-(α-morpholinoisobutyroyl)phenoxy]-methane,
1,2-bis[4-(α-morpholinoisobutyroyl)phenoxy]-ethane,
1,4-bis[4-(α-morpholinoisobutyroyl)phenoxy]-butane,
1,3-bis[4-(α-morpholinoisobutyroyl)phenoxy]-2-hydroxy-propane,
4,4'-bis(α-morpholinoisobutyroyl)-diphenyl oxide,
1,4-di-[4-(α-morpholinoisobutyroyl)-phenoxy]-benzene,
di-[4-(α-morpholinoisobutyroyl)-phenyl]-adipate,
di-[4-(α-morpholinoisobutyroyl)-phenyl]-2,2,4-trimethylhexane-1,6-dioate,
di-[4-(α-morpholinoisobutyroyl)-phenyl]-nonane-1,9-dioate,
di-[4-(α-morpholinoisobutyroyl)-phenyl]-oxalate,
dimethyl-di[4-(α-morpholinoisobutyroyl)-phenyl]-silane,
1,3-di[4-(α-morpholinoisobutyroyl)-phenyl]-1,1,3,3-tetramethyldisiloxane,
1-(4-methoxyphenyl)-2-methyl-2-pyrrolidinopropanone-1,
1-(4-methoxyphenyl)-2-methyl-2-oxazolidinopropanone-1,
1-(4-methoxyphenyl)-2-methyl-2-piperazinopropanone-1,
1-(4-methoxyphenyl)-2-methyl-2-(4-methylpiperazino)propanone-1,
1-(4-methoxyphenyl)-2-methyl-2-(2-methoxyethyl)aminopropanone-1,
1-(4-methoxyphenyl)-2-methyl-2-(2,6-dimethylmorpholino)propanone-1,
1-(4-methoxyphenyl)-2-methyl-2[4-(2-hydroxypropyl)-piperazino[propanone-1,
1-(4-(methoxyphenyl)-2-methyl-2-[4-(2-hydroxyethyl)-piperazino]propanone-1,
1-(4-methoxyphenyl)-2-methyl-2-dimethylaminopropanone-1,
1-(4-methoxyphenyl)-2-methyl-2-diethylaminopropanone-1,
1-(4-methoxyphenyl)-2-methyl-2-dibutylaminopropanone-1,
1-(4-methoxyphenyl)-2-methyl-2-(N-methylanilino)propanone-1,
1-(4-methoxyphenyl)-2-methyl-2-butylaminopropanone-1,
1-(4-methoxyphenyl)-2-methyl-2-di(2-ethylhexyl)aminopropanone-1,
1-(4-methoxyphenyl)-2-methyl-2-di(2-methoxyethyl)aminopropanone-1,
1-(4-ethoxyphenyl)-2-methyl-2-di(2-methoxyethyl)aminopropanone-1,
1-(3,4-dimethoxyphenyl)-2-methyl-2-di(2-methoxyethyl)aminopropanone-1,
1-(4-hydroxyphenyl)-2-methyl-2-di(2-methoxyethyl)aminopropanone-1,
1-(4-methoxyphenyl)-2-methyl-2-di(2-ethoxyethyl)aminopropanone-1,
1-(4-methoxybenzoyl)-1-di(2-methoxyethyl)aminocyclohexane,
1-(3,4-dimethoxybenzoyl)-1-di(2-methoxyethyl)aminocyclohexane,
1-(4-methoxyphenyl)-2-methyl-2-di(2-hydroxyethyl)aminopropanone-1,
1-(4-methoxyphenyl)-2-methyl-2-cyclohexylaminopropanone-1,
1-(4-methoxyphenyl)-2-methyl-2-N-methylcyclohexylaminobutanone-1,
1-(4-ethoxyphenyl)-2-methyl-2-dodecylaminopropanone-1,
1-[4-(2-hydroxyethoxy)phenyl]-2-methyl-2-dibenzylaminopropanone-1,
1-(4-methoxyphenyl)-2-methyl-2-dialhylaminopropanone-1,
1-(4-methoxyphenyl)-2-methyl-methyl-2-(2-hydroxyethyl)aminopropanone-1,
1-(4-phenoxyphenyl)-2-methyl-2-di(2-methoxyethyl)aminopropanone-1,
1-(4-phenoxyphenyl)-2-methyl-2-(4-methylpiperazino)propanone-1,
1-(4-hydroxybenzoyl)-1-morpholinocyclohexane,
1-(4-methoxyphenyl)-2-methyl-2-amino-propanone-1,
1-(3,4-dimethoxyphenyl)-2-methyl-2-isopropylaminopropanone-1,
1-(4-methoxyphenyl)-2-methyl-2-methylaminopropanone-1,
1-(4-methoxybenzoyl)-1-metylaminocyclopentane,
1-(4-methoxybenzoyl)-1-morpholinocyclopentane,
1-(4-methoxyphenyl)-2-methyl-2-(N-methyl-2-hydroxyethylamino)propanone-1, 1-(4-ethoxyphenyl)-2-ethyl-2-di(2-cyanoethyl)aminobutanone-1,
1-(4-isopropoxyphenyl)-2-methyl-2-di(2-carbethoxyethyl)aminobutanone-1,
1-[4-(2-hydroxyethoxy)phenyl]-2-methyl-2-(4-carbethoxyphenyl)aminopropanone-1,
1-(4-methoxyphenyl)-2-methyl-2-(2-methoxy-1-methylethylamino)propanone-1,
1-(4-methoxyphenyl)-2-methyl-2-[N-(2-hydroxypropyl)-2-methoxy-1-methylethylamino]-propanone-1,
1-(4-methoxyphenyl)-2-methyl-2-(N-methyl-4-carbomethoxyphenylamino)propanone-1,
1-[4-(2-hydroxyethoxy)-phenyl]-2-methyl-2-(3-chloro-4-ethylphenyl)-aminopropanone-1,
1(4-methoxyphenyl)-2-methyl-2-(2,5-dichloro-phenyl)aminopropanone-1,
1-(4-methoxyphenyl)-2-methyl-2-thiomorpholinopropanone-1,
1-(4-methoxphenyl)-2-methyl-2-[4-(2-carbethoxyethyl)piperazino]propanone-1,
2-(4-anisoyl)-2-methyl-pyrrolidine,
2-(4-anisoyl)-1-(2-hydroxyethyl)-2-methyl-pyrrolidine,
3,4-dimethyl-4-(3-propoxybenzoyl)oxazolidine,
1,2-dimethyl-2-(4-anisoyl)-piperidine,
3-(4-anisoyl)-3-methyl-1,2,3,4-tetrahydroisoquinoline,
3-(4-anisoyl)-3-benzyl-1,2,3,4-tetrahydroisoquinoline,
3-(3,4-dimethoxybenzoyl)-3-methyl-1,2,3,4-tetrahydroisoquinoline,
3-(4-anisoyl)-2,3-dimethyl-1,2,3,4-tetrahydroisoquinoline,
3-(3-propoxybenzoyl)-3-methyl-2-allyl-1,2,3,4-tetrahydroisoquinoline,
3-(4-ethoxybenzoyl)-3-methyl-2-(2-hydroxyethyl)-1,2,3,4-tetrahydroisoquinoline,
3-(3,4-dimethoxybenzoyl)-3-methyl-2-(2-hydroxyethyl)-1,2,3,4-tetrahydroisoquinoline,
3-(3,4-methylenedioxybenzoyl)-2,3-dimethyl-1,2,3,4-tetrahydroisoquinoline,
1-[4(cyanomethoxy)phenyl]-2-methyl-2-morpholinopropanone-1,
1-[4-(methallyloxy)phenyl]-2-methyl-2-morpholinopropanone-1,
1-(4-methoxyphenyl)-2-methyl-2-(N-methyl-2-hydroxypropylamino)propanone-1,
2-(4-anisoyl)-1,2-dimethyl-4-phenylpyrrolidine,
1-(4-methoxyphenyl)-2-methyl-2-morpholinobutanone-1,
1-(4-methoxyphenyl)-2-methyl-2-morpholinopentanone-1,
1-(4-methoxyphenyl)-2-ethyl-2-morpholinobutanone-1,
1-(4-methoxyphenyl)-2-ethyl-2-morpholinohexanone-1,
1-(4-methoxyphenyl)-2-propyl-2-morpholinopentanone-1,
1-(4-methoxyphenyl)-2-methyl-2-di(2-methoxyethyl)aminobutanone-1,
1-(4-methoxyphenyl)-2-methyl-2-di(2-methoxyethyl)aminopentanone-1,
1-(4-methoxyphenyl)-2-ethyl-2-di(2-methoxyethyl)aminobutanone-1,
1-[4-(2-hydroxyethoxy)phenyl]-2-methyl-2-morpholinobutanone-1,
1-[4-(2-hydroxyethoxy)phenyl]-2-methyl-2-morpholinopentanone-1,
1-[4-(2-hydroxyethoxy)phenyl]-2-ethyl-2-morpholinohexanone-1,
1-(4-hydroxyphenyl)-2-methyl-2-morpholinobutanone-1,
1-(4-hydroxyphenyl)-2-ethyl-2-morpholinobutanone-1,
1-(4-hydroxyphenyl)-2-propyl-2-morpholinopentanone-1,
1-(4-hydroxyphenyl)-2-ethyl-2-morpholinohexanone-1,
1-(4-hydroxybenzoyl)-1-morpholinocyclopentane,
1-[4-(2-hydroxyethoxy)benzoyl]-1-morpholinocyclohexane,
1-(4-methoxybenzoyl)-1-dimethylaminocyclohexane,
1-(4-methoxybenzoyl)-1-morpholinocyclopropane,
3-(4-methoxybenzoyl)-3-morpholinotetrahydropyrane,
4-(4-ethoxybenzoyl)-3,4-dimethyloxazolidine,
2-(4-ethoxybenzoyl)-1,2-dimethylpiperidine,
1-(4-methoxyphenyl)-2-morpholino-2-phenyl-propanone-1,
1-(4-methoxyphenyl)-2-diethylamino-2-phenyl-propanone-1,
1,2-bis(4-methoxyphenyl)-2-morpholinopropanone-1,
1-[4(2-hydroxyethoxy)phenyl]-2,2-diphenyl-2-morpholinoethanone-1,
1-(4-methoxyphenyl)-2-methyl-2,3-dimorpholinopropanone-1,
1-(3-methoxyphenyl)-3-methoxy-2-methyl-2-morpholinopropanone-1,
1-(4-methoxyphenyl)-2-methyl-2-morpholino-4-carbethoxybutanone-1,
1-(4-ethoxyphenyl)-2-methyl-2-morpholino-4-cyanobutanone-1,
1-[3-(2-hydroxyethoxy)phenyl]-2-methyl-2-morpholino-5-di(2-hydroxyethyl)aminopentanone-1,
1-(4-methoxyphenyl)-2-methyl-2-morpholinopenten-4-one-1,
1-(4-methoxyphenyl)-2-methyl-2-morpholino-3-phenylpropanone-1,
1-(4-methoxyphenyl)-2-benzyl-2-morpholino-3-phenylpropanone-1,
1-(2,3-dihydro-1,4-benzodioxin-6-yl)-2-methylmorpholinopropanone-1,
1-(2,3-dihydro-1,4-benzodioxin-6-yl)-2-methyl-2-di(methoxyethyl)aminopropanone-1,
1-(2,3-dihydro-1,4-benzodioxin-6-yl)-2-methyl-2-(4-methylpiperazino)pentanone-1,
1-(2,3-dihydro-1,4-benzodioxin-6-yl)-2-methyl-2-piperidinopropanone-1,
1-(1,3-benzodioxol-5-yl)-2-methyl-2-piperidinopropanone-1,
1-(1,3-benzodioxol-5-yl)-2-methyl-2-morpholinopropanone-1,
1-(1,3-benzodioxol-5-yl)-2-methyl-2-di(2-methoxyethyl)aminopropanone-1,
1-(1,3-benzodioxol-5-yl)-2-methyl-2-pyrrolidinopropanone-1,
1-(1,3-benzodioxol-5-yl)-2-methyl-2-pyrrolidinobutanone-1,
1-(1,3-benzodioxol-5-yl)-2-methyl-2-pyrrolidinopentanone-1,
1-(3,4-dihydro-2H-1,5-benzodioxepin-7-yl)-2-methyl-2-morpholinopropanone-1,
1-(2,3-dihydrobenzofuran-5-yl)-2-methyl-2-morpholinopropanone-1,
1-(2,3-dihydrobenzofuran-5-yl)-2-methyl-b 2-di(2-methoxyethyl)aminopropanone-1,
1-(2,3-dihydro-2-methyl-benzofuran-5-yl)-2-methyl-2-morpholinopropanone-1,
1-(2,3-dihydro-2-methylbenzofuran-5-yl)-2-methyl-2-di(2-methoxyethyl)aminopropanone-1,
1-(chroman-6-yl)-2-methyl-2-morpholinopropanone-1,
1-(dibenzofuran-2-yl)-2-methyl-2-morpholinopropanone-1, 1-(dibenzofuran-2-yl)-2-methyl-2-di(2-methoxyethyl)aminopropanone-1,
1-(dibenzofuran-2-yl)-2-methyl-2-piperidinopropanone-1,
1-(dibenzofuran-2-yl)-2-ethyl-2-morpholinohexanone-1,
1-(9H-xanthen-3-yl)-2-methyl-2morpholinopropanone-1,
1-(9H-xanthen-3-yl)-2-methyl-2-di(2-ethoxyethyl)aminopropanone-1,
1-(dibenzo[b,e][1,4]dioxin-2-yl)-2-methyl-2-morpholinopropanone-1,
1-(dibenzo[b,e][1,4]dioxin-2-yl)-2-methyl-2-di(2-methoxyethyl)aminopropanone-1,
1-(10,11-dihydro-dibenz[b,f]oxepin-2-yl)-2-methyl-2-morpholinopropanone-1,
2,8-bis(α-morpholinoisobutyroyl)-dibenzofuran,
2,8-bis[α-di(2-methoxyethyl)aminoisobutyroyl]-dibenzofuran,
2-(α-morpholino-isobutyroyl)-8-[α-(di-(2-methoxyethyl)amino)isobutyroyl]-dibenzofuran,
3,6-bis(α-morpholinoisobutyroyl)-9H-xanthene,
2,8-bis(α-morpholinoisobutyroyl)-dibenzo[b,e][1,4]dioxine,
2,8-bis(α-morpholinoisobutyroyl)-10,11-dihydrodibenz[b,f]oxepine,
1-(2-methoxyphenyl)-2-methyl-2-morpholinopropanone-1,
1-(3-methoxyphenyl)-2-methyl-2-morpholinopropanone-1,
1-(3,4-dimethoxyphenyl)-2-methyl-2-morpholinopropanone-1,
1-(4,5-dimethoxy-2-bromophenyl)-2-methyl-2-morpholinopropanone-1,
1-(4,5-dimethoxy-3-bromophenyl)-2-methyl-2-morpholinopropanone-1,
1-(2,4,6-trimethoxyphenyl)-2-methyl-2-morpholinopropanone-1,
1-(3,4,5-trimethoxyphenyl)-2-methyl-2-morpholinopropanone-1,
1-(2,4-dimethoxyphenyl)-2-methyl-2-morpholinopropanone-1,
1-(2,4,5-trimethoxyphenyl)-2-methyl-2-morpholinopropanone-1,
1-(2,3,4-trimethoxy-6-methylphenyl)-2-methyl-2-morpholinopropanone-1,
1-(2,5-dimethoxyphenyl)-2-methyl-2-morpholinopropanone-1,
1-(2,5-dimethoxy-3-bromophenyl)-2-methyl-2-morpholinopropanone-1,
1-(2,5-diethoxyphenyl)-2-methyl-2-morpholinopropanone-1,
1-(2,5-diethoxy-3-chlorophenyl)-2-methyl-2-morpholinopropanone-1,
1-(4-hydroxy-3-methoxyphenyl)-2-methyl-2-morpholinopropanone-1,
1-(4-acetoxy-3-methoxyphenyl)-2-methyl-2-morpholinopropanone-1,
1-[4-(trimethylsilyloxy)-3-methoxyphenyl]-2-methyl-2-morpholinopropanone-1,
1-[4-(1-ethoxyethoxy)-3-methoxyphenyl]-2-methyl-2-morpholinopropanone-1,
1-[4-(2-tetrahydropyranyloxy)-3-methoxyphenyl]-2-methyl-2-morpholinopropanone-1,
1-[4-(2-hydroxyethoxy)-3-methoxyphenyl]-2-methyl-2-morpholinopropanone-1,
1-(2-methoxy-5-methylphenyl)-2-methyl-2-morpholinopropanone-1,
1-(2-allyl-4,5-dimethoxyphenyl)-2-methyl-2-morpholinopropanone-1,
1-[2-methoxy-5-(prop-1-enyl)-phenyl]-2-methyl-2-morpholinopropanone-1,
1-(2,3-dichloro-4-methoxyphenyl)-2-methyl-2-morpholinopropanone-1,
1-(3-fluoro-4-methoxyphenyl)-2-methyl-2-morpholinopropanone-1,
1-(5-bromo-2-methoxyphenyl)-2-methyl-2-morpholinopropanone-1,
1-(5-chloro-2-methoxyphenyl)-2-methyl-2-morpholinopropanone-1,
1-[4-(2-bromoethoxy)phenyl]-2-methyl-2-morpholinopropanone-1,
1-[4-(3-bromopropoxy)phenyl]-2-methyl-2-morpholinopropanone-1,
1-[4-(2-morpholinoethoxy)phenyl]-2-methyl-2-morpholinopropanone-1,
1-[4-(2,3-epoxypropyloxy)phenyl]-2-methyl-2-piperidinopropanone-1,
1-[4-(2-hydroxyethoxy)phenyl]-2-methyl-2-di(2-methoxyethyl)aminopropanone-1,
1-(4-phenethyl)-2-methyl-2-di(2-methoxyethyl)aminopropanone-1,
1-(2-methyl-4-phenoxyphenyl)-2-methyl-2-piperidinopropanone-1,
2-methyl-4,4'-bis(α-morpholinoisobutyroyl)-diphenyl oxide,
4-(α-morpholinoisobutyroyl)-4'-[α-di(2-methoxyethyl)aminoisobutyroyl]-diphenyl oxide,
1-(4-hydroxyphenyl)-2-methyl-2-di(2-methoxyethyl)aminopropanone-1,
1-(3,5-dimethyl-4-hydroxyphenyl)-2-methyl-2-morpholinopropanone-1,
1-(3-tert.-butyl-4-hydroxy-5-methyl-phenyl)-2-methyl-2-morpholinopropanone-1,
1-(3,5-di-tert.-butyl-4-hydroxyphenyl)-2-methyl-2-morpholinopropanone-1,
1-(3-carbethoxy-4-hydroxyphenyl)-2-methyl-2-morpholinopropanone-1,
1-(3-carbethoxy-4-methoxyphenyl)-2-methyl-2-morpholinopropanone-1,
1-(3,4-dihydroxyphenyl)-2-methyl-2-morpholinopropanone-1,
1-(2,4-dihydroxyphenyl)-2-methyl-2-morpholinopropanone-1,
1-(2,5-dihydroxyphenyl)-2-methyl-2-morpholinopropanone-1,
1-(2,3,4-trihydroxyphenyl)-2-methyl-2-morpholinopropanone-1,
1-(2,3,4,5,6-pentamethoxy-phenyl)-2-methyl-2-morpholinopropanone-1,
1-[4-(2-hydroxyethoxy)phenyl]-2-amino-2-methylpropanone-1,
1-[3,4,5-tris-(2-hydroxyethoxy)phenyl]-2-methyl-2-morpholinopropanone-1,
1-[4-(2-ethoxypropyloxy)phenyl]-2-methyl-2-morpholinopropanone-1,
1-(4-methoxyphenyl)-2-methyl-2-di(2-methoxypropyl)aminopropanone-1,
1-(4-hydroxyphenyl)-2-methyl-2-di(2-hydroxypropyl)aminopropanone-1,
1-(4-methoxyphenyl)-2-methyl-2-di(2-butoxyethyl)aminopropanone-1,
7a(7H)-(4-anisoyl)-1H,3H,5H-oxazolo[3,4-c]oxazole,
1-[4-(2-acryloyloxyethoxy)phenyl]-2-methyl-2-morpholinopropanone-1, 1-[4-(2-propionyloxyethoxy)phenyl]-2-methyl-2-morpholinobutanone-1.

The following compounds are examples of photoinitiators of the formula II:

1,4-bis(4-methoxyphenyl)-2,3-dimethyl-2,3-dimorpholino-1,4-butanedione,
1,5-bis(4-methoxyphenyl)-2,4-dimethyl-2,4-dimorpholino-1,5-pentanedione,
1,6-bis[4-(2-hydroxypropyloxy)phenyl]-2,5-dimethyl-2,5-dimorpholino-1,6-hexanedione,
1,10-bis(4-phenethyl)-2,9-dibenzyl-2,9-dimorpholino-1,10-decanedione,
1,7-bis[3-(2-hydroxyethoxy)phenyl]-2,6-dimethyl-2,6-dimorpholino-4-oxa-1,7-pentanedione,
1,9-bis(3,4-methylenedioxyphenyl)-2,8-dimethyl-2,8-bis(N-methyl-2-methoxyethylamino)-5-oxa-1,9-nonanedione,
α,α'-bis(4-hydroxybenzoyl)-α,α'-bis-piperidino-1,4-diethylcyclohexane,
1,4-bis(4-anisoyl)-1,4-dimorpholinocyclohexane,
1,2-bis(4-anisoyl)-1,4-dimorpholinocyclohexene-4,
1-[4-(2-carbethoxyethoxy)benzoyl]-3-diethylamino-3-(4-hydroxybenzoyl)-1-morpholinocyclopentane,
2,3-bis-[4-(2-hydroxyethoxy)benzoyl]-2,3-bis(dimethylaminobicyclo[2.2.1]heptane,
2,3-bis(4-anisoyl)-2,3-dimorpholinobicyclo[2.2.1]heptene-5.

The following compounds are examples of photoinitiators of the formula III:

2,2'-(1,4-piperazinediyl)bis[1-(4-(2-hydroxyethoxy)phenyl-2-methylpropanone-1],
2,2'-(1,4-piperazinediyl)bis[1-(4-methoxyphenyl)-2-methylbutanone-1],
2,2'-(methylimino)bis[1-(4-methoxyphenyl)-2-methylpropanone-1],
2,2'-(benzylimino)bis[2-methyl-1-(4-phenethyl)-propanone-1],
2,2'-(2-hydroxyethylimino)bis[2-methyl-1(3,4-methylenedioxyphenyl)butanone-1],
1,8-bis-(3-methoxyphenyl)-3-(N)-ethyl-2,2,7,7-tetramethyl-3,6-diaza-1,8-octanedione,
1-[4-(2-hydroxyethoxy)phenyl]-12-(4-hydroxyphenyl)-3,10-bis(2-hydroxyethyl)-2,2,11,11-tetramethyl-3,10-diaza-1,12-dodecanedione,
N,N'-bis[1-(4-anisoyl)cyclohexyl]-N,N'-dimethyl-1,3-diaminopropane.

Some of the compounds of the formulae I, II and III are known compounds, the genral preparation of which is described in European Patent Application Publication No. 3002. Others are novel compounds which likewise form subject matter of the present invention. These are compounds of the formulae I, II and III in which Ar is an oxygen-containing aromatic radical, selected from the following formulae:

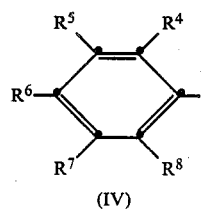

(IV)

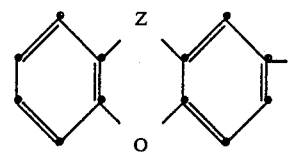

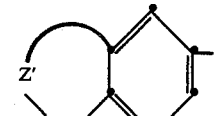

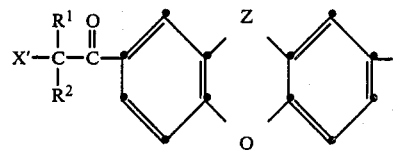

wherein
Z is a direct bond, —CH$_2$, —CH$_2$CH$_2$— or —O—,
Z' is —CH$_2$CH$_2$— or —(CH$_2$)$_3$—, each unsubstituted or substituted by CH$_3$,
R$^4$, R$^5$, R$^6$, R$^7$ and R$^8$ independently of one another are hydrogen, halogen, C$_1$-C$_4$-alkyl, C$_3$-C$_{12}$-alkenyl, C$_5$-C$_6$-cycloalkyl, phenyl, —COOH, —COO(C$_1$-C$_4$-alkyl), —OH or —OR$^9$, with the proviso however that at least one of the radicals R$^4$ to R$^8$ is a group —OH or —OR$^9$,
R$^9$ is C$_1$-C$_{12}$-alkyl, C$_3$-C$_{12}$-alkenyl, cyclohexyl, hydroxycyclohexyl, C$_1$-C$_4$-alkyl which is substituted by one or more of the groups Cl, Br, CN, SH, —N(-C$_1$-C$_4$-alkyl)$_2$, piperidino, morpholino, OH, —O(C$_1$-C$_4$-alkyl), —OCH$_2$CH$_2$CN, —OCH$_2$CH$_2$COO(C$_1$-C$_4$-alkyl), —OOC—R$^{10}$, —COOH, —COO(C$_1$-C$_8$-alkyl), —CONH(C$_1$-C$_4$-alkyl), —CON(C$_1$-C$_4$-alkyl)$_2$,

—CO—(C$_1$-C$_4$-alkyl) or —CO—phenyl, or is 2,3-epoxypropyl, —(CH$_2$CH$_2$O)$_q$—H, phenyl, C$_7$-C$_9$-phenylalkyl, C$_7$-C$_9$-phenylhydroxyalkyl, phenyl which is substituted by halogen, C$_1$-C$_4$-alkyl, C$_1$-C$_4$-alkoxy or —COO(C$_1$-C$_4$-alkyl), or is tetrahydropyranyl, tetrahydrofuranyl, a group —CO—R$^{10}$, —COO(C$_1$-C$_8$-alkyl), —CONH(C$_1$-C$_4$-alkyl), —CON(C$_1$-C$_4$-alkyl), —CON(C$_1$-C$_4$-alkyl)$_2$, —Si(R$^{15}$)(R$^{16}$)$_2$, —SO$_2$—R$^{17}$ or a radical of the formula

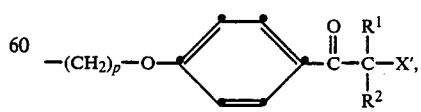

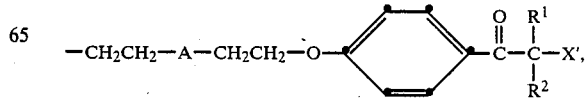

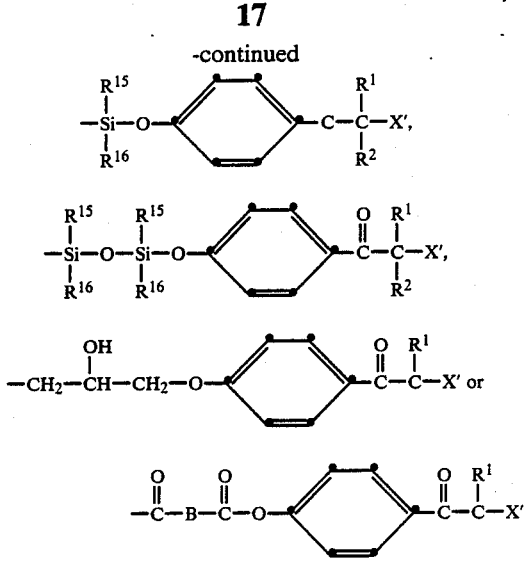

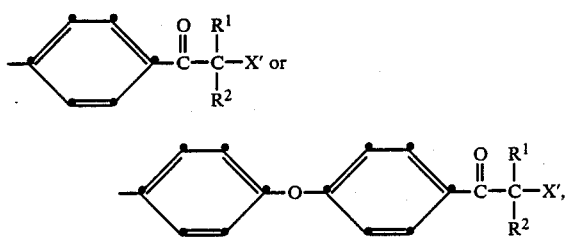

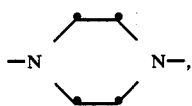

wherein p is 1 to 4, q is 2 to 20, A is oxygen or sulfur, and B is a direct bond or a $C_1$–$C_{10}$-alkylene radical, or $R^9$ is a radical of the formula $R^{10}$ is $C_1$–$C_4$-alkyl, $C_2$–$C_4$-alkenyl or phenyl,
X and X' are an amino group —$N(R^{11})(R^{12})$,
Y is a divalent radical of the formula —$N(R^{13})$— or —$N(R^{13})$—$(CH_2)_x$—$N(R^{13'})$—,
wherein x is 1 to 8,
$R^{11}$ is $C_1$–$C_{12}$-alkyl, $C_2$–$C_4$-alkyl which is substituted by one or more of the groups OH, $C_1$–$C_4$-alkoxy, CN or —COO($C_1$–$C_4$-alkyl), or is $C_3$–$C_5$-alkenyl, cyclohexyl, $C_7$–$C_9$-phenylalkyl, phenyl or phenyl substituted by Cl, $C_1$–$C_4$-alkyl, OH, $C_1$–$C_4$-alkoxy or —COO($C_1$–$C_4$-alkyl), or $R^{11}$ and $R^1$ together are the group —$CH_2OCH_2$—,
$R^{12}$ has one of the meanings given for $R^{11}$ or together with $R^{11}$ is $C_5$–$C_7$-alkylene, or $C_3$–$C_7$-alkylene which is interrupted by —O—, —S— or —$N(R^{14})$, or $R^{12}$ together with $R^2$ is $C_1$–$C_8$-alkylene, $C_7$–$C_{10}$-phenylalkylene or $C_2$–$C_4$-oxaalkylene or azaalkylene,
$R^{13}$ and $R^{13'}$ are hydrogen, $C_1$–$C_{12}$-alkyl, $C_1$–$C_4$-hydroxyalkyl, cyclohexyl or benzyl,
$R^{14}$ is hydrogen, $C_1$–$C_4$-alkyl, $C_1$–$C_4$-hydroxyalkyl, —$CH_2CH_2CN$ or —$CH_2CH_2COO(C_1$–$C_4$-alkyl),
$R^{15}$ and $R^{16}$ are $C_1$–$C_4$-alkyl or phenyl,
$R^{17}$ is $C_1$–$C_{18}$-alkyl, phenyl or $C_7$–$C_{20}$-alkylphenyl,
Ar' has one of the meanings given for Ar,
$R^1$ and $R^2$ independently of one another are each $C_1$–$C_8$-alkyl, $C_1$–$C_4$-alkyl which is substituted by OH, $C_1$–$C_4$-alkoxy, CN, —COO($C_1$–$C_8$-alkyl) or —$N(R^{11})(R^{12})$, or are allyl, phenyl, chlorophenyl, $R^9$—O—phenyl or $C_7$–$C_9$-phenylalkyl, or $R^1$ and $R^2$ together are $C_2$–$C_8$-alkylene, $C_3$–$C_9$-oxaalkylene or azaalkylene,
$R^3$ is a direct bond, $C_1$–$C_6$-alkylene, $C_2$–$C_6$-oxaalkylene or cyclohexylene, or together with the two substituents $R^2$ and the two C atoms to which these substituents are attached forms a cyclopentane, cyclohexane, cyclohexene, endomethylenecyclohexane or endomethylenecyclohexene ring,
and the acid addition salts of these compounds, with the reservation that, in the case of compounds of the formula I in which $R^1$ and $R^2$ are methyl and Ar is 4-methoxyphenyl or 4-phenoxyphenyl, X is not a piperidino radical.

Preferred compounds amongst these are those of the formula I in which Ar is a phenyl radical substituted in the 4-position by a group —$OR^9$. Particularly preferred are the compounds of the formula I in which Ar is a phenyl radical substituted in the 4-position by the group —$OR^9$, $R^9$ is $C_1$–$C_8$-alkyl, $C_3$–$C_6$-alkenyl, cyclohexyl, benzyl, phenyl, tolyl or one of the groups, —$CH_2CH_2OH$, —$CH_2CH_2$—OOC—CH=$CH_2$, —$CH_2$—COO($C_1$–$C_4$-alkyl), —$CH_2CH_2$—COO($C_1$–$C_4$-alkyl),

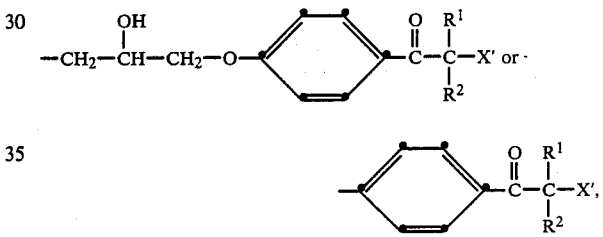

$R^1$ and $R^2$ are $C_1$–$C_4$-alkyl, or $R^1$ and $R^2$ together are $C_4$–$C_5$-alkylene, and X and X' are a morpholino radical or a radical of the formula —$N(CH_2CH_2$—$OCH_3)_2$.

The compounds of the formula I can be produced, using methods analogous to those known from the European Patent Application, Publication No. 3002, by introduction of the amino group into a corresponding aryl haloalkyl ketone V in accordance with the following reaction stages:

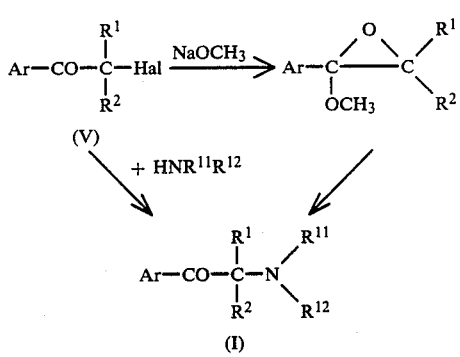

In these formulae Hal is halogen, in particular chlorine or bromine. If there is used in the final reaction stage half a mole of a primary amine $R^{13}NH_2$, or piperazine or a di-secondary diamine $R^{13}NH$—$(CH_2)_x$-

—NHR[13], there are obtained the corresponding compounds of the formula III.

The compounds of the formula II can be produced, in a manner analogous to that in which compounds of the formula I are obtained, by using, as starting material, diketones of the general formula Va

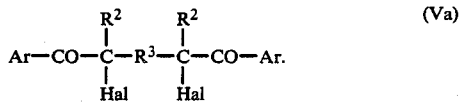

The haloalkyl ketones V can be produced from the corresponding aryl-alkyl ketones Ar—CO—CH(R[1])(R[2]) by the customary methods of α-halogenation of ketones. Alternatively, they can be obtained also from the aromatic compounds ArH by a Friedel-Crafts reaction with an α-halocarboxylic acid halide Hal—C(R[1])(R[2])—COHal.

The dihalodiketones Va can be produced analogously by α-halogenation of the corresponding diketones, or by a Friedel-Crafts reaction with an α,α'dihalodicarboxylic acid halide.

In the production of compounds of the formula I, II or III in which Ar is a phenyl radical substituted by the group —OH, by the method described in the foregoing, it is advisable to protect the phenolic OH group by a protecting group before halogenation, for example by an ether group, acyl group or sulfonyl group. This protecting group can then be removed by hydrolysis after amination. The same applies for compounds having the —OR[9] group, when there is a risk that R[9] will react with halogen. In this case, the phenol group is firstly protected by a protecting group, the protecting group is removed after halogenation and amination and, as the final step, the radical R[9] is introduced by the customary methods of etherification or esterification of phenolic hydroxyl groups, preferably by reaction with the corresponding halide R[9]Hal.

When R[9] is a radical —(CH$_2$CH$_2$O)$_q$—H, this is introduced by reaction with ethylene oxide. As tetrahydropyranyl or tetrahydrofuranyl radical, R[9] can be introduced by the acid-catalysed addition of dihydropyrane or dihydrofuran to the phenolic OH group. In an analogous manner, also vinyl ether, acrylonitrile and acrylic acid ester can be added by an acid- or base-catalysed reaction, by which means there are obtained compounds in which R[9] is an ethyl radical substituted by alkoxy, cyano or —COO(C$_1$-C$_8$-alkyl).

A further possibility for producing compounds of the formula I is the reaction of α-aminoalkyl nitriles with the corresponding aryllithium compounds:

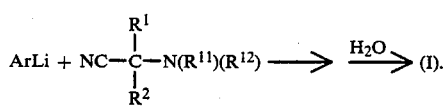

Compounds of the formula II or III can be produced from the corresponding dinitriles in an analogous manner.

Compounds of the formula I in which X is an —NH$_2$ or —NHR[10] group can, alternatively, be produced in an intramolecular Houben-Hoesch reaction, from the corresponding benzylaminoacetonitriles, by cyclisation in concentrated sulfuric acid to the imidazolines VI, according to D. N. Harcourt, N. Taylor, R. D. Waigh, J. Chem. Res. (S), 1978, 154; and subsequent hydrolysis of VI by the method of M. R. Euerby and R. D. Waigh, J. Chem. Res. (S), 1982, 240:

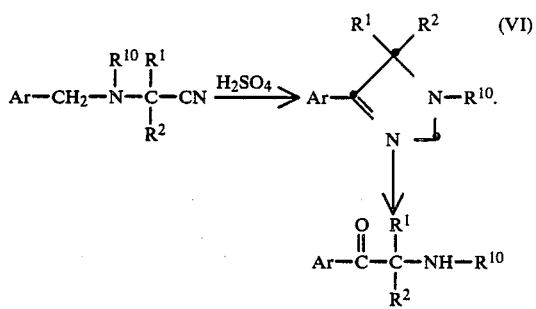

The acid addition salts of the compounds I, II and III can be produced in the customary manner from the aminoketones by neutralisation with a protonic acid. Examples of such acids are: HCl, HBr, H$_3$PO$_4$, H$_2$SO$_4$, toluenesulfonic acid, dodecylbenzenesulfonic acid, methanesulfonic acid, hexadecanesulfonic acid, HBF$_4$ or HPF$_6$.

Further details regarding the synthesis of compounds of the formulae I, II and III can be learnt from the following production examples.

EXAMPLE A

Production of aminoketones by way of the α-haloketones (A$_1$) 4-Methoxy-isobutyrophenone 160 g (1.2 mols) of finely powdered aluminium chloride are placed into 500 ml of tetrachloroethylene and cooled to 0°–5° C. To the white suspension is added dropwise a mixture of 108 g (1.0 mol) of anisole and 117 g (1.1 mols) of isobutyric acid chloride. At unchanged temperature, the mixture is subsequently allowed to react for 3 hours with vigorous stirring, and the thickly liquid, yellowish suspension is then poured into icewater. The organic phase is separated, dried over sodium sulfate and concentrated in a rotary evaporator. The residue is purified by vacuum distillation to thus obtain 171 g (96% of theory) of colourless liquid having a boiling point of 84° C. at 3.4 mbar.

The NMR spectrum is compatible with the given structure.

NMR (CDCl$_3$), δ (ppm): 1.17 (d, 6H, J=7 Hz); 3.43 (m, 1H); 3.73 (s, 3H); 6.77 and 7.77 (AA'BB' system, J$_{AB}$=9 Hz, J$_{AB'}$≦1 Hz, 4H).

(A$_2$) 4-Methoxy-α-bromoisobutyrophenone 178 g (1 mol) of 4-methoxyisobutyrophenone are placed into 300 ml of chlorobenzene, and 160 mg (1 mol) of bromine are added dropwise at room temperature with stirring. After completion of the dropwise addition, the mixture is allowed to react for 3 hours, and residues of the formed HBr gas are subsequently expelled from the solution with a stream of nitrogen. The solvent is then removed in a rotary evaporator at a bath temperature of 40° C. There remain as residue 257 g (100% of theory) of the α-bromoketone in the form of yellowish-brown oil, which can be used without further purification for the next reaction.

The NMR spectrum of the crude product is compatible with the given structure.

NMR (CDCl₃), δ (ppm): 1.99 (s, 6H); 3.72 (s, 3H); 6.71 and 8.01 (AA'BB' system, $J_{AB}=9$ Hz, $J_{AB'} \leq 1$ Hz, 4H).

(A₃)
2-Methoxy-2-(4-methoxyphenyl)-3,3-dimethyloxirane

A solution of 70 g (1.3 mols) of sodium methoxide in 170 g of methanol is taken at room temperature and, with vigorous stirring, 257 g (1 mol) of the crude bromoketone from A₂ are added dropwise. The temperature is kept at 20°-25° C. by slight cooling. After the dropwise addition has been completed, stirring is continued for 2 hours; the formed white suspension is then diluted with 200 ml of toluene, and the sodium bromide which has precipitated is filtered off. The filtrate is concentrated in the rotary evaporator, in the course of which further sodium bromide precipitates. After renewed filtration the crude product is purified by vacuum distillation. The yield is 180 g (86% of theory) of the epoxyether in the form of a colourless liquid which boils at 64° C./2.5 mbar, m.p. 41°-43° C. The NMR spectrum is compatible with the given structure.

NMR (CDCl₃), δ (ppm): 0.97 (s, 3H); 1.49 (s, 3H); 3.10 (s, 3H); 3.70 (s, 3H); 6.73 and 7.19 (AA'BB' system, $J_{AB}=8.5$ Hz, $J_{AB'} \leq 1$ Hz, 4H).

(A₄)
1-(4-methoxyphenyl)-2-methyl-2-morpholinopropanone-1

208 g (1 mol) of the epoxyether from A₃) are refluxed in 348 g (4 mols) of morpholine for 12 hours, the forming methanol being continuously distilled off. The cooled solution is concentrated in a rotary evaporator, and the residue is recrystallised from hexane. There are obtained 237 g of the pure product as colourless crystals, m.p. 75°-76° C. The NMR spectrum is compatible with the given structure.

NMR (CDCl₃), δ (ppm): 1.28 (s, 6H); 2.52 (m, 4H); 3.61 (m, 4H); 3.77 (s, 3H); 6.73 and 8.41 (AA'BB' system, $J_{AB}=9$ Hz, $J_{AB'} \leq 1$ Hz, 4H).

| Elementary analysis: | C | H | N | O |
|---|---|---|---|---|
| calculated: | 68.42 | 8.04 | 5.32 | 18.23% |
| found: | 68.19 | 8.06 | 5.33 | 18.25% |

The aminoketones given in Table I are produced in an analogous manner.

TABLE 1

| Compound No. | Formula | Physical data °C. | Elementary analysis (%) | | |
|---|---|---|---|---|---|
| | | | C | H | N |
| 1 | CH₃O–C₆H₄–CO–C(CH₃)₂–N(morpholine) | m.p. 75–76° | cal. 68.42<br>found 68.19 | 8.04<br>8.06 | 5.32<br>5.33 |
| 2 | CH₃O–C₆H₄–CO–C(CH₃)₂–N(piperidine) | b.p. 180° | cal. 73.53<br>found 72.7 | 8.87<br>9.0 | 5.36<br>5.3 |
| 3 | C₆H₅–O–C₆H₄–CO–C(CH₃)₂–N(morpholine) | m.p. 99–101° | cal. 73.82<br>found 73.51 | 7.13<br>7.01 | 4.31<br>4.42 |
| 4 | C₆H₅–O–C₆H₄–CO–C(CH₃)₂–N(piperidine) | b.p.₀.₁ 180° | cal. 77.99<br>found 77.7 | 7.80<br>7.7 | 4.33<br>3.5 |
| 5 | dibenzofuranyl–CO–C(CH₃)₂–N(morpholine) | m.p. 140–141° | cal. 74.28<br>found 74.3 | 6.55<br>6.6 | 4.33<br>4.4 |
| 6 | CH₃O–C₆H₄–CO–C(CH₃)₂–N(CH₂CH₂OCH₃)₂ | liquid | cal. 65.99<br>found 65.93 | 8.80<br>8.76 | 4.53<br>4.48 |
| 7 | CH₃O–C₆H₄–CO–C(CH₃)₂–N(N-methylpiperazine) | m.p. 62–64° | cal. 69.53<br>found 69.24 | 8.75<br>8.70 | 10.14<br>10.16 |

TABLE 1-continued

| Compound No. | Formula | Physical data °C. | Elementary analysis (%) | | | |
|---|---|---|---|---|---|---|
| | | | | C | H | N |
| 8 | CH₃O—C₆H₄—CO—C(CH₃)₂—N(morpholine NH) | oil | cal. found | 68.67 68.46 | 8.45 8.67 | 10.68 10.43 |
| 9 | CH₃O—C₆H₄—CO—C(CH₃)₂—N(CH₃)—CH₂CH₂OH | m.p. 89–92° | cal. found | 66.91 66.77 | 8.42 8.34 | 5.57 5.52 |
| 10 | CH₃O—C₆H₄—CO—C(CH₃)₂—N(n-C₄H₉)₂ | oil | cal. found | 74.71 74.71 | 10.23 10.27 | 4.61 4.61 |
| 11 | CH₃O—C₆H₄—CO—C(CH₃)₂—N(CH₃)₂ | oil | cal. found | 70.56 70.53 | 8.65 8.85 | 6.33 6.29 |
| 12 | CH₃O—C₆H₄—CO—C(CH₃)₂—NH—CH(CH₃)—CH₂OCH₃ | liquid | cal. found | 66.91 66.86 | 8.42 8.41 | 5.57 5.49 |
| 13 | CH₃O—C₆H₄—CO—C(CH₃)₂—NH—CH₂CH₂OCH₃ | liquid | cal. found | 67.90 67.90 | 8.74 8.68 | 5.28 4.99 |
| 14 | CH₃O—C₆H₄—CO—C(CH₃)₂—N(2,6-dimethylmorpholine) | viscous | cal. found | 70.07 69.83 | 8.65 8.54 | 4.81 4.72 |
| 15 | CH₃O—C₆H₄—CO—C(C₂H₅)(CH₃)—N(morpholine) | viscous | cal. found | 69.29 69.08 | 8.36 8.38 | 5.05 5.09 |
| 16 | CH₃O—C₆H₄—CO—C(C₄H₉)(C₂H₅)—N(morpholine) | m.p. 74–76° | cal. found | 71.44 71.39 | 9.15 9.03 | 4.38 4.26 |
| 17 | 3,4-(CH₃O)₂—C₆H₃—CO—C(CH₃)₂—N(morpholine) | m.p. 84–87° | cal. found | 65.51 66.24 | 7.90 7.87 | 4.77 4.54 |
| 18 | 3,4-(CH₃O)₂—C₆H₃—CO—C(CH₃)₂—N(morpholine) | viscous | cal. found | 65.51 65.51 | 7.90 7.85 | 4.77 4.79 |

TABLE 1-continued

| Compound No. | Formula | Physical data °C. | Elementary analysis (%) | | |
|---|---|---|---|---|---|
| | | | C | H | N |
| 18a | C₄H₉O—⟨phenyl⟩—CO—C(CH₃)₂—N⟨morpholine⟩O | m.p. 91–93° | cal. 70.79<br>found 70.77 | 8.91<br>8.86 | 4.59<br>4.65 |

(A₅) Chlorination with copper-II chloride 1-(3,4-Dimethoxyphenyl)-2-chloro-2-methylpropanone-1

79.1 g (0.38 mol) of 1-(3,4-dimethoxyphenyl)-2-methylpropanone-1, produced analogously to Example A₁, are dissolved in 400 ml of an isopropanol/water mixture 4:1, and 64.8 g (0.38 mol) of copper-II chloride (dihydrate) are then added. The suspension is heated to the reflux temperature (about 80° C.), and the green solution becomes darker. After 8 hours, a further 64.8 g (0.38 mol) of copper-II chloride are added. The dark-green suspension is refluxed for a further 21 hours, and is afterwards cooled and filtered. The filtrate is diluted with 300 ml of toluene, and the toluene solution is extracted three times with 200 ml of water. The toluene solution is dried with sodium sulfate and concentrated by evaporation. The crude product obtained is examined by means of gas-chromatography and NMR spectrum, and then further processed, in a manner analogous to that of Example A₃, to the corresponding oxirane.

EXAMPLE B

Production of the free phenol by ether cleavage 1-(4,hydroxyphenyl-2-methyl-2-morpholinopropanone-1

131.7 g (0.5 mol) of 1-(4-methoxyphenyl)-2-methyl-2-morpholinopropanone-1 are dissolved in 300 ml of hydrobromic acid (about 47%), and the solution is stirred at 120° C. for 24 hours. It is subsequently cooled, and neutralised with concentrated sodium hydroxide solution to pH 8.5. The formed suspension is repeatedly extracted with diethyl ether. The ether is dried, and concentrated by evaporation, and the crystals remaining behind are recrystallised from a methanol/water mixture (5:1). The yield is 89 g of colourless crystals, m.p. 189°–192° C. (compound No. 19). The NMR spectrum is compatible with the given structure.

NMR (CDCl₃/CH₃OD), δ (ppm): 1.30 (s, 6H); 2.55 (m, 4H); 3.64 (m, 4H); 4.32 (s, broad, 1H); 6.69 and 8.31 (AA'BB' system, $J_{AB}$=9 Hz, $J_{AB'}$≦1 Hz, 4H).

| Elementary analysis: | C | H | N |
|---|---|---|---|
| calculated: | 67.45 | 7.65 | 5.62 |
| found: | 67.47 | 7.67 | 5.61. |

EXAMPLE C

Silylation of the free phenol

1-[4-(Trimethylsilyloxy)phenyl]-2-methyl-2-morpholinopropanone-1

To a suspension of 15.0 g (0.06 mol) of 1-(4-hydroxyphenyl)-2-methyl-2-morpholinopropanone-1 in 50 ml of toluene are added 3.6 g of hexamethyldisilazane and 0.2 g of 4-dimethylaminopyridine. There are then added dropwise at room temperature 2.3 g of trimethylchlorosilane, and the suspension is stirred overnight. The ammonium chloride which has precipitated is filtered off, and subsequently washed with toluene. The solution is concentrated in a vacuum rotary evaporator. The yield is 18.0 g of a light-yellow oil which solidifies in the cold state in crystalline form, m.p. 59°–64° C. (compound No. 20). The NMR spectrum is compatible with the given structure.

NMR (CDCl₃), δ (ppm): 0.32 (s, 9H); 1.29 (s, 6H); 2.50 (m, 4H); 3.60 (m, 4H); 6.75 and 8.43 (AA'BB' system, $J_{AB}$=9 Hz, $J_{AB'}$≦1 Hz, 4H).

| Elementary analysis | C | H | N |
|---|---|---|---|
| calculated: | 63.51 | 8.47 | 4.36% |
| found: | 63.40 | 8.52 | 4.48%. |

EXAMPLE D

Etherification of the free phenol

1-[4-(Allyloxy)phenyl]-2-methyl-2-morpholinopropanone-1

6.7 g (0.055 mol) of allyl bromide are added dropwise, at room temperature, to a suspension of 12.5 g (0.05 mol) of 1-(4-hydroxyphenyl)-2-methyl-2-morpholinopropanone-1 and 7.6 g of powdered potassium carbonate in 30 ml of acetone. The mixture is heated to 60° C. and stirred overnight at this temperature. The suspension is then cooled, diluted with 100 ml of toluene and filtered. The solution is concentrated in a vacuum rotary evaporator and diluted again with 100 ml of toluene. The toluene solution is extracted with water, dried with potassium carbonate and concentrated in a vacuum rotary evaporator. There are thus obtained 14 g of a yellow oil (compound No. 21). The NMR spectrum is compatible with the given structure.

NMR (CCl₄), δ (ppm): 1.21 (s, 6H); 2.42 (m, 4H); 3.50 (m, 4H); 4.35–4.58 (m, 2H); 4.98–5.45 (m, 2H); 5.58–6.23 (m, 1H); 6.69 and 8.32 (AA'BB' system, $J_{AB}$=9 Hz, $J_{AB'}$≦1 Hz, 4H).

| Elementary analysis: | C | H | N |
|---|---|---|---|
| calculated: | 70.56 | 8.01 | 4.84% |
| found: | 70.56 | 8.09 | 4.83%. |

EXAMPLE E

Esterification of the free phenol 1-(4-Acetoxyphenyl)-2-methyl-2-morpholinopropanone-1

12.5 g (0.05 mol) of 1-(4-hydroxyphenyl)-2-methyl-2-morpholinopropanone-1, 6.2 g (0.06 mol) of acetic anhydride and 0.3 g (about 5 mol %) of dimethylaminopyridine are suspended in 50 ml of dioxane, and the suspension is stirred for two hours. There are then added dropwise 6.1 g (0.06 mol) of triethylamine and, after one hour's stirring, the formed solution is concentrated in a vacuum rotary evaporator; the residue is subsequently dissolved in 100 ml of toluene, and the solution is precipitated portionwise by the addition of 300 ml of hexane. The crystals are filtered off, washed with hexane and dried. The result is 13.3 g of white crystals, m.p. 100°–103° C. (compound No. 22). The NMR spectrum is compatible with the given structure.

NMR (CCl$_4$), δ (ppm): 1.24 (s, 6H); 2.20 (s, 3H); 2.46 (m, 4H); 3.53 (m, 4H); 6.94 and 8.38 (AA'BB' system, $J_{AB}$=9 Hz, $J_{AB'}\leq$1 Hz, 4H).

EXAMPLE F

N-Hydroxyalkylation 1-(4-Methoxyphenyl)-2-methyl-2-[4-(2hydroxypropyl)-piperazino]-propanone-1

8.9 g (0.034 mol) of 1-(4-methoxyphenyl)-2-methyl-2-piperazinopropanone-1 are dissolved in 50 ml of methanol, and the solution is cooled to 0° C. There is then added 0.5 g of $CO_2$ as dry ice, and there are subsequently added dropwise 2.17 g (0.037 mol) of propylene oxide. The solution is stirred for about 17 hours at room temperature, and afterwards concentrated in the rotary evaporator to leave 10.9 g of oil, which slowly solidifies into the form of a wax-like compound (compound No. 23). The structure

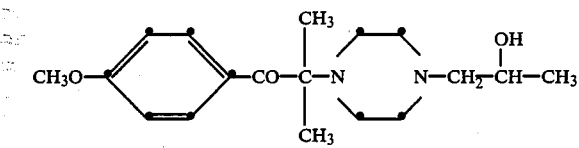

is confirmed by the NMR spectrum.

NMR (CCl$_4$), δ (ppm): 1.02 (d, 3H); 1.23 (s, 6H), 2.0–2.9 (m, 10H); 3.2–3.9 (m, 2H); 3.75 (s, 3H); 6.69 and 8.32 (AA'BB' system, $J_{AB}$=9 Hz, $J_{AB'}\leq$1 Hz, 4H).

There is produced in an analogous manner from 1-(4-methoxyphenyl)-2-methyl-2-(2-methoxyethyl)amino-propanone-1, with propylene oxide, 1-(4-methoxyphenyl)-2-methyl-2-[N-(2-hydroxypropyl)-N-(2-methoxyethyl)amino]propanone-1, which is obtained as liquid (compound No. 24). The structure

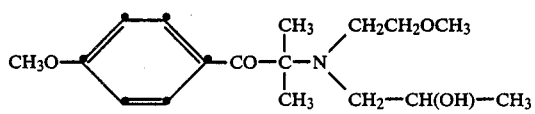

is confirmed by the NMR spectrum.

NMR (CCl$_4$), δ (ppm): 0.9–1.2 (m, 3H); 1.33 (s, 6H); 2.4–2.6 (m, 6H); 3.13 (s, 3H); 3.1–3.5 (m, 4H); 3.65 (s, 3H); 6.63 and 8.15 (AA'BB' system, $J_{AB}$=9 Hz, $J_{AB'}\leq$1 Hz, 4H).

EXAMPLE G

Salt formation

4-Dodecylbenzenesulfonate of 1-(4-methoxyphenyl)-2-methyl-2-morpholinopropanone-1

6.58 g (0.025 mol) of 1-(4-methoxyphenyl)-2-methyl-2-morpholinopropanone-1 are dissolved in 20 ml of absolute ether. There are then dissolved 8.16 g (0.025 mol) of commercial 4-dodecylbenzenesulfonic acid (Marlon ®AS$_3$ acid, C. W. Hüls AG) in 20 ml of ether, and the solution is added dropwise at room temperature, with cooling, to the amine. The white suspension which precipitates is filtered off and subsequently washed with 50 ml of absolute ether. The crystals are dried at 50° C., m.p. 118°–123° C. (compound (compound No. 25).

| Elementary analysis: (589.83) | C | H | N | S |
|---|---|---|---|---|
| calculated: | 67.20 | 8.72 | 2.37 | 5.44% |
| found: | 66.69 | 8.61 | 2.30 | 5.47%. |

The pigmented compositions according to the invention contain an olefinically unsaturated, photopolymerisable binder. The binder can consist of one or more unsaturated compounds; it contains preferably two or three unsaturated compounds. In addition, the binder can contain other film-forming components which are not unsaturated and do not therefore participate in the polymerisation. The unsaturated compounds can contain one or more olefinic double bonds. They can be of low molecular weight (monomeric) or of a higher molecular weight (oligomeric). Examples of monomers containing one double bond are alkyl acrylates or methacrylates or hydroxyalkyl acrylates or methacrylates, for example methyl, ethyl, butyl, 2-ethylhexyl or 2-hydroxyethyl acrylate, isobornyl acrylate or methyl or ethyl methacrylate. Further examples of the monomers are acrylonitrile, acrylamide, methacrylamide N-substituted (meth)acrylamides, vinyl esters, such as vinyl acetate, vinyl ethers, such as isobutyl vinyl ether, styrene, alkylstyrenes, halogenostyrenes, N-vinylpyrrolidone, vinyl chloride or vinylidene chloride.

Examples of monomers containing several double bonds are ethylene glycol diacrylate, propylene glycol diacrylate, neopentylglycol diacrylate, hexamethyleneglycol diacrylate or bisphenol A diacrylate, 4,4'-bis-(2-acryloyloxyethoxy)diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris-(2-acryloyloxyethyl)isocyanuate.

Examples of polyunsaturated compounds of higher molecular weight (oligomers) are acrylated epoxide resins, acrylated polyethers, acrylated polyurethanes or acrylated polyesters. Further examples of unsaturated oligomers are unsaturated polyester resins, which in most cases are prepared from maleic acid, phthalic acid and one or more diols and which have molecular weights of about 500 to 3,000. Unsaturated oligomers of this type can also be designated as prepolymers.

The binders for the photocurable compositions according to the invention can be, for example, a mixture of a monounsaturated and a polyunsaturated monomer.

In most cases, however, two-component mixtures of a prepolymer containing a polyunsaturated monomer, or three-component mixtures which also contain, in addition, a monounsaturated monomer, are used. In this respect the prepolymer primarily determines the properties of the lacquer film; by varying it those skilled in the art can influence the properties of the cured film. The polyunsaturated monomer functions as a crosslinking agent, which makes the lacquer film insoluble. The monounsaturated monomer functions as a reactive diluent by means of which the viscosity is reduced without the necessity of using a solvent.

Two-component and three-component systems of this type based on a prepolymer are used for printing inks as well as for lacquers, photoresists and other coloured, photocurable compositions. One-component systems based on photocurable prepolymers are also frequently used as binders for printing inks.

Unsaturated polyester resins are in most cases used in two-component systems together with a monounsaturated monomer, preferably styrene. Specific one-component systems, for example polymaleimides or polychalcones, are often used for photoresists.

The binder can additionally contain non-photopolymerisable, film-forming components. These can be, for example, polymers which dry physically or solutions thereof in organic solvents, for example nitrocellulose or cellulose acetobutyrate. These can, however, also be chemically curable or heat-curable resins, for example polyisocyanates, polyepoxides or melamine resins. The concomitant use of heat-curable resins is important for use in so-called hybrid systems, which are photopolymerised in a first stage and are crosslinked in a second stage by subsequent heat treatment.

The photocurable compositions according to the invention contain a pigment or a dye. They preferably contain a pigment. The pigment can be an inorganic pigment, for example titanium dioxide (rutile or anatase), iron yellow, iron red, chrome yellow, chrome green, nickel-titanium yellow, ultramarine blue, cobalt blue, cadmium yellow, cadmium red or zinc white. The pigment can be an organic pigment, for example a monoazo or bisazo pigment or a metal complex thereof, a phthalocyanine pigment or a polycyclic pigment, for example a perylene, thioindigo, flavanthrone, quinacridone, tetrachloroisoindolinone or triphenylmethane pigment. The pigment can also be a carbon black or a metal powder, for example aluminium or copper powder. The pigment can also be a mixture of two or more different pigments, such as is customary for achieving specific colour shades.

The pigment can be present in an amount of 5 to 60% by weight, based on the total composition; 10-30% of pigment is present in most cases in printing inks.

Dyes are frequently also used for imparting colour instead of pigments in photoresists or reprographic films. These can be organic dyes belonging to a very wide variety of classes, for example azo dyes, methine dyes, anthraquinone dyes or metal complex dyes. In the concentrations used, these dyes are soluble in the particular binders. The customary concentrations are 0.1 to 20%, preferably 1–5%, by weight, based on the total composition.

Problems similar to those in the radiation curing of coloured compositions can also arise in the radiation curing of uncoloured compositions containing a filler. In these cases too, the photoinitiators described above can be used with success. Examples of compositions of this type are metal primers, priming coats and surface fillers. Examples of fillers in compositions of this type are kaolin, talc, barytes, gypsum, chalk or silicate fillers.

In addition to the three essential components (binder, pigment and photoinitiator), the photopolymerisable composition can contain further constituents which depend especially on the intended field of use. Whereas solvent-free compositions are preferred for most purposes, it can be necessary to add a solvent in order to achieve the viscosity required for the coating. The customary lacquer solvents, which are frequently mixtures of different solvents, are suitable for this purpose. Flow control auxiliaries, thixotropic agents or wetting agents can also be added to achieve a uniform coating. Waxes or other lubricants are frequently added in the case of printing inks. The photopolymerisable composition can also be in the form of an aqueous dispersion or solution.

Although the compositions according to the invention have an excellent stability to storage in the dark, it can be useful for certain purposes, for example for use in tropical countries, to add polymerisation inhibitors. Examples of inhibitors used for this purpose are hydroquinone and derivatives thereof, $\beta$-naphthols, sterically hindered phenols, copper compounds, compounds of trivalent phosphorus, phenothiazine, quaternary ammonium compounds or hydroxylamine derivative.

Conversely, chain transfer agents, such as tertiary amines or thiol compounds, can be added in order to accelerate UV curing or to achieve specific physical properties. The addition of free radical initiators, such as peroxides or other organic per-compounds and benzpinacol or other organic compounds which can be split by heat, can also accelerate photopolymerisation in specific cases.

The compositions according to the invention can also contain a photosensitiser which displaces the spectral sensitivity into specific ranges. This can, for example, be an organic dye, perylene or a derivative of anthracene or thioxanthone. Thioxanthone derivatives, for example alkylthioxanthones or thioxanthonecarboxylic acid esters, in particular, effect a considerable acceleration of photopolymerisation, as sensitisers.

It is preferable to use only one compound of the formula I, II or III as a photoinitiator. However, in specific cases it can be advantageous to use a mixture of two such compounds or a mixture with another known photoinitiator. The quantity of photoinitiator required in the photocurable coloured composition is 0.1–20% by weight, preferably 1–6% by weight.

The compositions according to the invention can be used for various purposes. The most important and preferred use is for printing inks. These can be printing inks for offset printing, letterpress printing, gravure printing, screen printing or flexographic printing. The printing inks according to the invention are particularly suitable for offset printing, screen printing and gravure printing.

A second important field of use is their use for paints. Pigmented coatings are used, in particular, as a primer for protecting metals from corrosion, but are also used as coloured top lacquers for decorative purposes on all possible substrates, for example metal, wood, cardboard, plastics or textiles. The use of compositions according to the invention for white lacquers and for black-pigmented metal primers is of particular interest. Aqueous systems can also be used as electrophoretically deposable lacquers.

Further fields of use are the radiation curing of photoresists, the photo-crosslinking of silver-free films or other fields of photographic reproduction.

In all these uses the photocurable composition is applied in a thin layer to a substrate. If a solvent was present, this is then substantially removed, for example by heating in a drying oven, by passing warm air over the substrate or by infrared irradiation or microwave irradiation. The dried layer is then irradiated with shortwave light, preferably with UV light within the wavelength range of 250–400 nm. Examples of light sources suitable for this purpose are medium-pressure, high-pressure and low-pressure mercury lamps and also super-actinic fluorescent tubes. The radiation curing is preferably carried out in a continuous process, the material to be cured being conveyed past and beneath the source of radiation. The transport speed is decisive for the production rate of the article; it depends on the irradiation time required. For this reason, the acceleration of radiation curing by photoinitiators is an important factor in the production of such articles, and it is one of the advantages of the photoinitiators of the formulae I, II and III that they ensure rapid curing even in a low concentration and even in the case of compositions having a high pigment content.

If a hybrid system is used as the binder, the curing of the film can be carried out in two stages. For example, a prepolymer is produced by radiation polymerisation of the photopolymerisable components, and this is then completely cured by a thermal condensation reaction of the components capable of undergoing condensation. A two-stage procedure of this type can be of interest, for example, for coating or bonding operations, and also in curing relatively thick layers.

Another two-stage process is the combination of electron irradiation and UV irradiation, which is also of interest for fairly thick layers. Whereas the electron radiation effects curing in the depth of the film, the surface is cured by the UV irradiation.

The examples which follow illustrate the properties and applicability of the photocurable compositions according to the invention. In these examples the parts and percentages are by weight.

EXAMPLE 1

A blue printing ink is prepared in accordance with the following formulation:
62 parts of Satalin®AP 565 (urethane acrylate resin made by Synthese, Holland),
15 parts of 4,4'-di-($\beta$-acryloyloxyethoxy)-2,2-diphenylpropane (Ebecryl®150, UCB, Belgium) and
23 parts of Irgalithblau®GLSM (Ciba-Geigy AG, Basel).

The mixture is homogenised on a triple roll mill and ground to a particle size of $5<\mu$.

5 g portions of this printing ink are mixed to form a homogenous mixture with the desired quantity of photoinitiator on a disc grinding machine under a pressure of 180 kg/m$^2$, while cooling with water.

Offset prints on strips of art printing paper measuring 4×20 cm are made with this printing ink, using a test printing apparatus (made by Prüfbaum, Federal Republic of Germany). The printing conditions are:
coating of printing ink: 1.5 g/m$^2$
applied pressure: 25 kg/cm$^2$
printing speed: 1 m/second
A printing roller with a metal surface (aluminium) is used.

The printed samples are irradiated in a UV irradiation apparatus (QC processor made by RPC, USA) with 2 lamps each with an output of 80 watt/cm and a distance from the lamp of 11 cm. The irradiation time is varied by varying the transport speed of the samples.

The surface drying of the printing ink is tested by the so-called transfer test immediately after irradiation. This is effected by pressing a white paper onto the printed sample under a pressure of 25 kg/cm$^2$. If the paper remains colourless the test is successful. If visible quantities of colour are transferred to the test strips, this is a sign that the surface of the sample is not yet adequately cured.

Table 2 shows the maximum transport speed at which the transfer test was still successful.

The completeness of cure of the printing ink is tested by again preparing offset prints as described above, but using printing rollers having a rubber surface and printing the metal side of aluminium-coated paper strips.

Irradiation is carried out as described above. Immediately after irradiation, the completeness of the cure is tested in an REL apparatus for testing complete curing. In this test, an aluminium cylinder covered with cloth is placed on the printed sample and rotated about its own axis once under a pressure of 220 g/cm$^2$ in the course of 10 seconds. If visible damage takes place on the sample in the course of this, the completeness of the curing of the printing ink is inadequate. Table 2 shows the maximum transport speed at which the REL test was still successful.

TABLE 2

| Photoinitiator | | | |
|---|---|---|---|
| | | Maximum transport speed (m/minute) | |
| Compound No. | Quantity (% by weight) | Transfer test (surface curing) | REL test (complete curing) |
| 1 | 3 | >170 | 120 |
|   | 6 | >170 | >170 |
| 6 | 3 | >170 | 80 |
|   | 6 | >170 | 160 |
| 7 | 3 | 160 | 80 |
|   | 6 | >170 | 170 |
| 8 | 3 | 150 | 90 |
|   | 6 | >170 | 130 |
| 10 | 3 | 60 | 20 |
|    | 6 | 160 | 70 |
| 11 | 3 | 90 | 40 |
|    | 6 | >170 | 110 |
| 12 | 3 | 30 | 30 |
|    | 6 | 120 | 60 |
| 14 | 3 | 140 | 70 |
|    | 6 | 170 | 150 |
| 15 | 3 | >170 | 90 |
|    | 6 | >170 | >170 |
| 18 | 3 | 30 | 30 |
|    | 6 | 130 | 60 |
| 20 | 3 | 130 | 70 |
|    | 6 | >170 | 90 |
| 21 | 3 | >170 | 90 |
|    | 6 | >170 | 150 |
| 23 | 3 | 100 | 50 |
|    | 6 | >170 | 110 |

EXAMPLE 2

The concomitant use of the thioxanthones as sensitisers.

A white lacquer is prepared in accordance with the following formulation:
17.6 g of Ebecryl®593 (polyester acrylate resin made by UCB, Belgium)
11.8 g of N-vinylpyrrolidone,
19.6 g of titanium dioxide RTC-2 (titanium dioxide made by Tioxide, England),
19.6 g of Sachtolith®HDA (lithopone made by Sachtleben Chemie, West Germany),
11.8 g of trimethylolpropane trisacrylate and
19.6 g of Setalux®UV 2276 (acrylated epoxide resin based on bisphenol A, Kunstharzfabrik Synthese, Holland).

The above components, together with 125 g of glass beads (diameter 4 cm) are ground to a particle size $\leq 5$ $\mu$m in a 250 ml glass bottle for at least 24 hours.

The stock paste thus obtained is divided into portions and each portion is mixed with the photoinitiators and photosensitisers (co-initiators) indicated in Table 3, by stirring at 60° C., and the mixtures are ground with glass beads for a further 16 hours.

The white lacquers thus prepared are applied to sheets of glass in a thickness of 30 μm, using a doctor blade. The samples are exposed to light in a single passage in a PPG irradiation apparatus with one or two lamps each having an output of 80 watt/cm. The speed of passage of the samples through the irradiation apparatus is raised continuously until adequate curing no longer takes place. The maximum speed of which a lacquer film which is still resistant to wiping is formed, is shown in Table 3 as "rate of curing".

The following compounds are used in this test:
photoinitiator

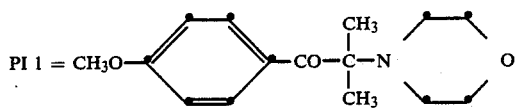

photosensitiser

PS 1 = 2-isopropylthioxanthone

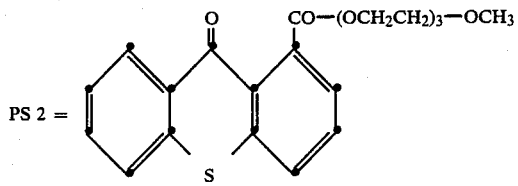

PS 3 = 2-methyl-6-ethoxycarbonyl-thioxanthone

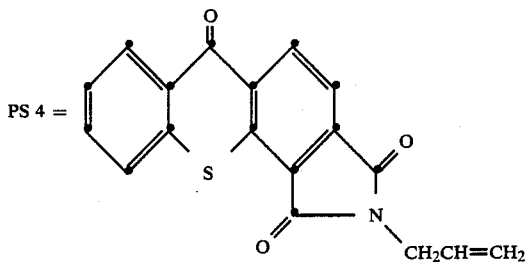

TABLE 3

| Photo-initiator | Co-initiator (sensitiser) | Rate of curing 80 W/cm | Rate of curing 160 W/cm |
|---|---|---|---|
| 2% PI 1 | — | 10 m/min | 10 m/min |
| 2% PI 1 | 0,25% PS 1 | 30 m/min | 70 m/min |
| 2% PI 1 | 0,25% PS 2 | 20 m/min | 40 m/min |
| 2% PI 1 | 0,25% PS 3 | 70 m/min | 150 m/min |
| 2% PI 1 | 0,25% PS 4 | 90 m/min | >170 m/min |

It can be seen from the table that even small quantities of the sensitiser accelerate the rate of curing considerably.

What is claimed is:

1. A compound of the formula I

in which Ar is an oxygen-containing aromatic radical of the formula:

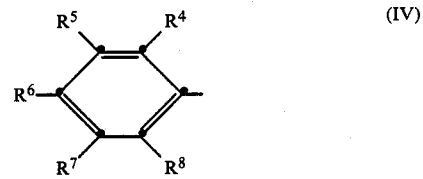

wherein
$R^4$, $R^5$, $R^6$, $R^7$ and $R^8$ independently of one another are each hydrogen halogen, $C_1$-$C_4$-alkyl, $C_3$-$C_{12}$-alkenyl, $C_5$-$C_6$-cycloalkyl, phenyl, —OH or —$OR^9$, with the proviso however that at least one of the radicals $R^4$ to $R^8$ is an —$OR^9$ group, $R^9$ is $C_3$-$C_{12}$-alkenyl, cyclohexyl, or hydroxycyclohexyl, X is morpholino or N($C_2$-$C_4$ alkyl substituted by $C_1$-$C_4$ alkoxy)$_2$, $R^1$ and $R^2$ independently of one another are each $C_1$-$C_8$-alkyl, or $R^1$ and $R^2$ together are $C_5$-$C_8$-alkylene, or an acid addition salt of such a compound.

2. A compound of the formula I according to claim 1, wherein Ar is a phenyl radical which is substituted in the 4-position by a group —$OR^9$.

3. A compound of the formula I according to claim 1, wherein Ar is a phenyl radical substituted in the 4-position by a group —$OR^9$, $R^9$ is $C_3$-$C_6$-alkenyl or cyclohexyl, $R^1$ and $R^2$ are $C_1$-$C_4$-alkyl, or $R^1$ and $R^2$ together are $C_4$-$C_5$-alkylene, and X is a morpholino radical or a radical of the formula —N($CH_2CH_2$—$OCH_3$)$_2$.

4. A compound according to claim 1 of the formula

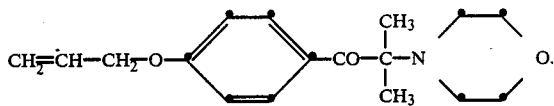

* * * * *